US012727768B2

(12) United States Patent
Saraf et al.

(10) Patent No.: US 12,727,768 B2
(45) Date of Patent: Sep. 8, 2026

(54) PHONOCARDIOGRAM (PCG) SIGNAL PROCESSING SYSTEMS AND METHODS FOR DETERMINING CARDIAC TISSUE AND VALVULAR BLOOD FLOW PARAMETERS

(71) Applicants: THE REGENTS OF THE UNIVERSITY OF CALIFORNIA, Oakland, CA (US); SENSYDIA CORPORATION, Los Angeles, CA (US)

(72) Inventors: Kanav Saraf, Los Angeles, CA (US); Per Henrik Borgstrom, Charlestown, MA (US); Christopher Inhwan Baek, Playa Vista, CA (US); Michael Wasko, Los Angeles, CA (US); Yi Zheng, Los Angeles, CA (US); Xu Zhang, Irvine, CA (US); William J. Kaiser, Los Angeles, CA (US); Aman Mahajan, Pittsburgh, PA (US)

(73) Assignees: THE REGENTS OF THE UNIVERSITY OF CALIFORNIA, Oakland, CA (US); SENSYDIA CORPORATION, Los Angeles, CA (US)

( * ) Notice: Subject to any disclaimer, the term of this patent is extended or adjusted under 35 U.S.C. 154(b) by 654 days.

(21) Appl. No.: 18/300,904

(22) Filed: Apr. 14, 2023

(65) Prior Publication Data

US 2023/0329563 A1 Oct. 19, 2023

Related U.S. Application Data

(60) Provisional application No. 63/332,074, filed on Apr. 18, 2022.

(51) Int. Cl.
*A61B 5/02* (2006.01)
*A61B 5/346* (2021.01)
*A61B 5/00* (2006.01)

(52) U.S. Cl.
CPC .......... *A61B 5/02028* (2013.01); *A61B 5/346* (2021.01); *A61B 5/7267* (2013.01)

(58) Field of Classification Search
CPC .... A61B 5/02028; A61B 5/346; A61B 5/7267
See application file for complete search history.

(56) References Cited

U.S. PATENT DOCUMENTS 8,473,041 B2 6/2013 Bartnik
8,515,201 B1 8/2013 Murray Herrera
(Continued)

FOREIGN PATENT DOCUMENTS

CN 201244022 5/2009
CN 106456017 2/2017
WO 2022211972 A1 10/2022

OTHER PUBLICATIONS

Saraf, Kanav, et al., "Fully Automated Heart Disease Diagnosis and Evaluation using a Phonocardiogram-Based System", Philosophy in Bioengineering, University of California Theses and Dissertations, 2020, pp. 1-49.
(Continued)

*Primary Examiner* — Lindsey G Wehrheim
(74) *Attorney, Agent, or Firm* — O'BANION & RITCHEY LLP; John P. O'Banion

(57) ABSTRACT

A non-invasive, passive, and fully automated heart-sound-based system and method that provides estimates for blood velocity, tissue motion, and cardiac chamber size parameters for cardiac assessment is provided. The system uses a computer processor and software to receive PCG acoustic signals from one or more sensors and simultaneously receive electrocardiogram (ECG) signals from one or more sensors
(Continued)

that are attached to a patient. The phonocardiogram (PCG) processing system and methods compute proxy metrics for echocardiographic parameters of cardiac tissue motion and valvular blood flow for evaluation.

23 Claims, 10 Drawing Sheets

(56) References Cited

U.S. PATENT DOCUMENTS

| | | | |
|---|---|---|---|
| 8,771,195 B2 | 7/2014 | Kim | |
| 8,892,196 B2 | 11/2014 | Chang | |
| 10,959,629 B2 | 3/2021 | Kaiser | |
| 11,234,601 B2 | 2/2022 | Kaiser | |
| 2003/0144702 A1 | 7/2003 | Yu | |
| 2003/0208240 A1 | 11/2003 | Pastore | |
| 2004/0230129 A1* | 11/2004 | Haefner | A61N 1/36585 600/510 |
| 2005/0177062 A1 | 8/2005 | Skrabal | |
| 2008/0001735 A1 | 1/2008 | Tran | |
| 2008/0154144 A1 | 6/2008 | Unver | |
| 2008/0167566 A1 | 7/2008 | Unver | |
| 2009/0030292 A1 | 1/2009 | Bartnik | |
| 2009/0209875 A1 | 8/2009 | Giorgis | |
| 2011/0152638 A1 | 6/2011 | Bartnik | |
| 2014/0094870 A1 | 4/2014 | Renesto | |
| 2015/0011842 A1 | 1/2015 | Steinberg-Shapira | |
| 2016/0019914 A1 | 1/2016 | Sugiyama | |
| 2016/0038041 A1 | 2/2016 | Clinton | |
| 2016/0175598 A1 | 6/2016 | Volpe | |
| 2016/0270738 A1 | 9/2016 | Volpe | |
| 2018/0125376 A1 | 5/2018 | Denney, Jr. | |
| 2018/0160917 A1 | 6/2018 | Liu | |
| 2018/0168473 A1 | 6/2018 | Du | |
| 2019/0059747 A1 | 2/2019 | Kaiser | |
| 2019/0059748 A1 | 2/2019 | Kaiser | |
| 2019/0133516 A1 | 5/2019 | Banet | |
| 2020/0170527 A1 | 6/2020 | Kale | |

OTHER PUBLICATIONS

ISA/US, United States Patent and Trademark Office (USPTO), International Search Report and Written Opinion issued Jul. 13, 2023, related PCT international application No. PCT/US2022/018644, pp. 1-7, claims searched, pp. 8-15.

Ari, Sule, et al., "A robust heart sound segmentation algorithm for commonly occurring heart valve diseases." Journal of Medical Engineering & Technology, vol. 32, Issue 6, 2008, pp. 456-465.

Balaney, Bhavna, et al., "Invasive Validation of the Echocardiographic Assessment of Left Ventricular Filling Pressures using the 2016 Diastolic Guidelines: Head-to-Head Comparison with the 2009 Guidelines." Journal of the American Society of Echocardiography, vol. 31, Issue 1, 2018, pp. 79-88.

Borgstrom, Nils Peter, UCLA Electronic Theses and Dissertations, "The Integrated CardioRespiratory Heart Function Monitoring System", 2017, 1 page, first published Oct. 12, 2019, declaration of publication date from ProQuest, pp. 2-5, dissertation, pp. 6-154.

Dugundji, J., "Envelopes and pre-envelopes of real waveforms." IRE Transactions on Information Theory, vol. 4, Issue 1, 1958, pp. 53-57.

Eddleman, JR, E. E. et al., "The use of the systolic time intervals for predicting left ventricular ejection fracion in ischemic heart disease", American Heart Journal, vol. 93, No. 4, Apr. 1977, pp. 450-454.

Elgendi, Mohamed, et al., "The Voice of the Heart: Vowel-Like Sound in Pulmonary Artery Hypertension," Diseases, vol. 6, No. 2, 2018, p. 26.

European Patent Office (EPO), extended European search report issued Apr. 19, 2021, related European patent application No. 18851186.9, pp. 1-11, claims searched, pp. 12-16.

European Patent Office (EPO), extended European search report issued Apr. 30, 2021, related European patent application No. 18851588.6, pp. 1-13, claims searched, pp. 14-18.

Feigenbaum, Harvey. "Echocardiography: an overview." Journal of the American College of Cardiology, 1983, vol. 1, pp. 216-224.

Garrard, Clifford L, Jr. et al., "The Relationship of Alterations in Systolic Time Intervals to Ejection Fraction in Patients with Cardiac Disease", Circulation, vol. XLII, Sep. 1970, pp. 455-462.

Gill, D. et al., "Detection and Identification of Heart Sounds Using Homomorphic Envelogram and Self-Organizing Probabilistic Model", Computers in Cardiology, 2005: 32:957-960.

Illsar, et al., "The relationship between pulmonary artery capillary wedge pressure for the diagnosis of pulmonary vasculary disease, heart, lung and circulation", vol. 19, Issue 1, Jan. 2010, pp. 38-42.

ISA/US, United States Patent and Trademark Office (USPTO), International Search Report and Written Opinion issued Jun. 8, 2022, related PCT international application No. PCT/US2022/018951, pp. 1-11, with claims searched 12-17.

ISA/US, United States Patent and Trademark Office (USPTO), International Search Report and Written Opinion issued Oct. 19, 2018, related PCT international application No. PCT/US2018/046575, pp. 1-9, claims searched, pp. 10-13.

ISA/US, United States Patent and Trademark Office (USPTO), International Search Report and Written Opinion issued Oct. 24, 2018, related PCT international application No. PCT/US2018/046378, pp. 1-10, claims searched, pp. 11-16.

Johnson, Thomas V. et al., "Improvement in the Assessment of Diastolic Function in a Clinical Echocardiography Laboratory Following Implementation of a Quality Improvement Initiative." Journal of the American Society of Echocardiography, 2011, vol. 24, Issue 11, pp. 1169-1179.

Karnath, Bernard, et al., "Auscultation of the heart." Hospital Physician, Sep. 2002, pp. 39-45.

Liang, H., et al., "Heart sound segmentation algorithm based on heart sound envelogram." Computers in Cardiology, 1997. pp. 105-108.

Moyers, Brian et al., "Performance of Phonoelectrocardiographic left Ventricular Systolic Time Intervals and B-Type Natriuretic Peptide Levels in the Diagnosis of Left Ventricular Dysfunction", A.N.E., Apr. 2007, vol. 12, No. 2, pp. 89-97.

Nagueh, Sherif F. et al., "Recommendations for the Evaluation of Left Ventricular Diastolic Function by Echocardiography: An Udate from the American Society of Echocardiography and the European Association of Cardiovascular Imaging", European Journal of Echocardiography 17, 2016, pp. 1321-1360.

Nishimura, Rick A., et al., "Evaluation of Diastolic Filling of Left Ventricle in Health and Disease: Doppler Echocardiography Is the Clinician's Rosetta Stone." Journal of the American College of Cardiology vol. 30, Issue 1. 1997, pp. 8-18.

Pan, Y.N., et al., "Spectral Entropy: A Complementary Index for Rolling Element Bearing Performance Degradation Assessment." Proceedings of the Institution of Mech. Engineers, Part C: Journal of Mechanical Engineering Science, vol. 223, Issue 5, 2009, pp. 1223-1231.

Pelech, Andrew N., "The Physiology of Cardiac Auscultation," Pediatric Clinics of North America, vol. 51, No. 6, 2004, pp. 1515-1535.

Picard, Michael H., et al., "American Society of Echocardiography Recommendations for Quality Echocardiography aboratory Operations." Journal of the American Society of Echocardiography, vol. 24, Issue 1, Jan. 2011, pp. 1-10.

Saraf, Kanav et al., "Assessment of Left Ventricular Diastolic Function using Phonocardiogram Signals: A Comparison with Echocardiography", Annu Int Conf IEEE Eng Med Biol Soc. 2020, Jul. 2020:4067-4070.

Saraf, Kanav et al., "Fully-Automated Diagnosis of Aortic Stenosis Using Phonocardiogram-Based Features", Annu Int Conf IEEE Eng Med Biol Soc. 2019, Jul. 2019:6673-6676.

State Intellectual Property Office of the People's Republic of China, The first office action Issued Feb. 16, 2022, related Chinese patent application No. 2018880054490.X, Chinese-language document, pp. 1-11, English-language translation, pp. 12-23, claims examined, pp. 24-29.

(56) References Cited

OTHER PUBLICATIONS

Tranulis, et al., “Estimation of pulmonary arterial pressure by a neural network analysis using features based on time-frequency representations of the second heart sound”, Med. Biol. Eng. Comput., 40(2), Mar. 2002, pp. 205-212.
U.S. Food and Drug Administration, “Integrated CardioRespiratory System”, Letter to Anna Libman, Sensydia, Inc. dated Jun. 8, 2018, downloaded from Internet at https://www.accessdata.fda.gov/cdrh_docs/pdf17/K173156.pdf.
Upadhyay, Navneet, et al., “Speech enhancement using spectral subtraction-type algorithms: A comparison and simulation study.” Procedia Computer Science, vol. 54, 2015, pp. 574-584.
Yancy, Clyde W. et al, “2013 ACCF/AHA Guideline for the Management of Heart Failure: A Report of the American College of Cardiology Foundation/American Heart Association Task Force on Practice Guidelines.” Journal of the American College of Cardiology, Feb. 27, 2003, pp. 1-88.
Yeh, Yun-Chi et al., “QRS complexes detection for ECG signal: The Difference Operation Method”, Computer Methods and Programs in Biomedicine 91 (2008) 245-254.
Yeh, Yun-Chi, et al., “QRS complexes detection for ECG signal: The Difference Operation Method.” Computer Methods and Programs in Biomedicine vol. 91, 2008, pp. 245-254.

* cited by examiner

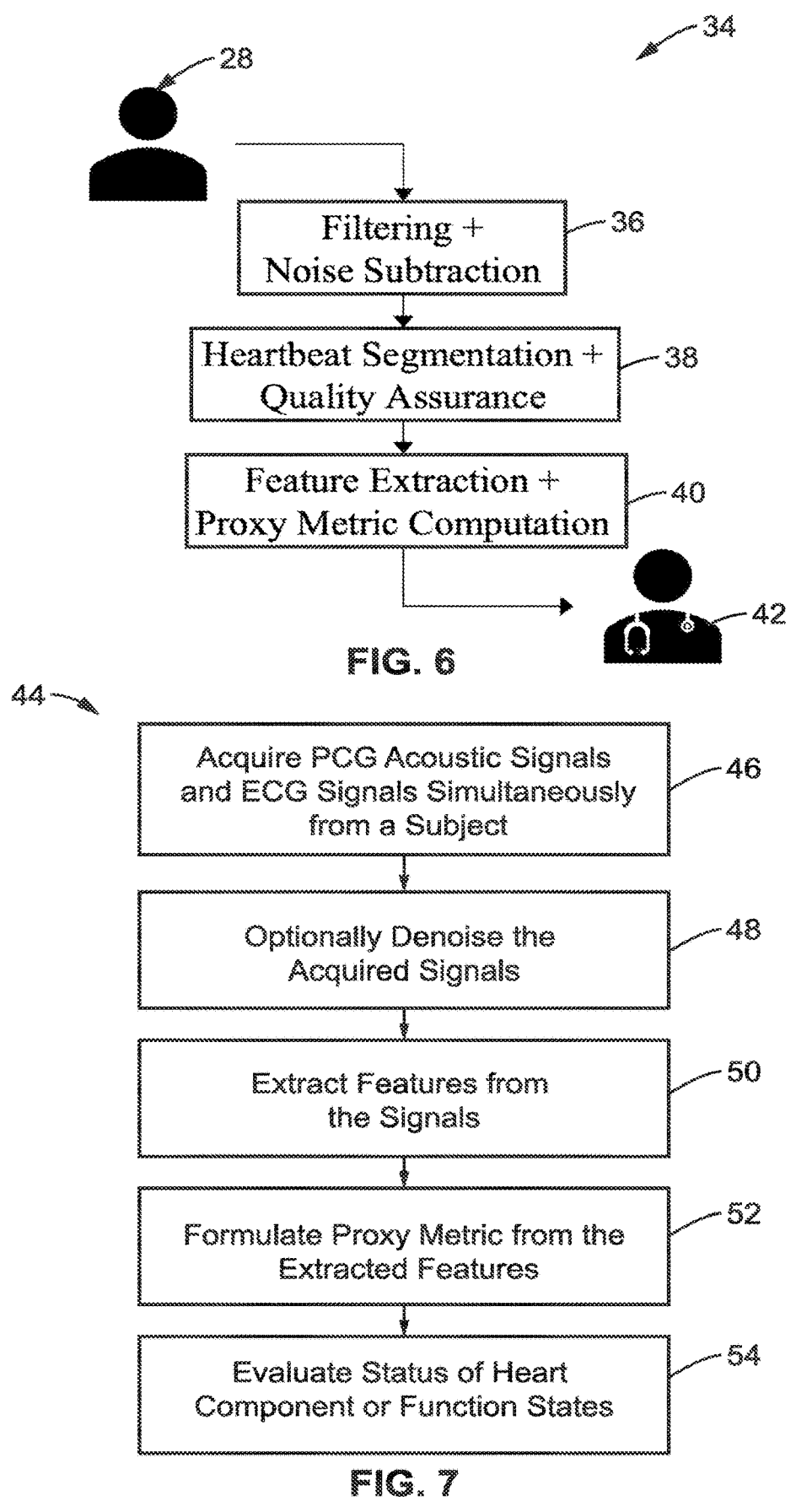

34

28

Filtering + Noise Subtraction — 36

Heartbeat Segmentation + Quality Assurance — 38

Feature Extraction + Proxy Metric Computation — 40

Acquire PCG Acoustic Signals and ECG Signals Simultaneously from a Subject — 46

Optionally Denoise the Acquired Signals — 48

Extract Features from the Signals — 50

Formulate Proxy Metric from the Extracted Features — 52

Evaluate Status of Heart Component or Function States — 54

FIG. 7

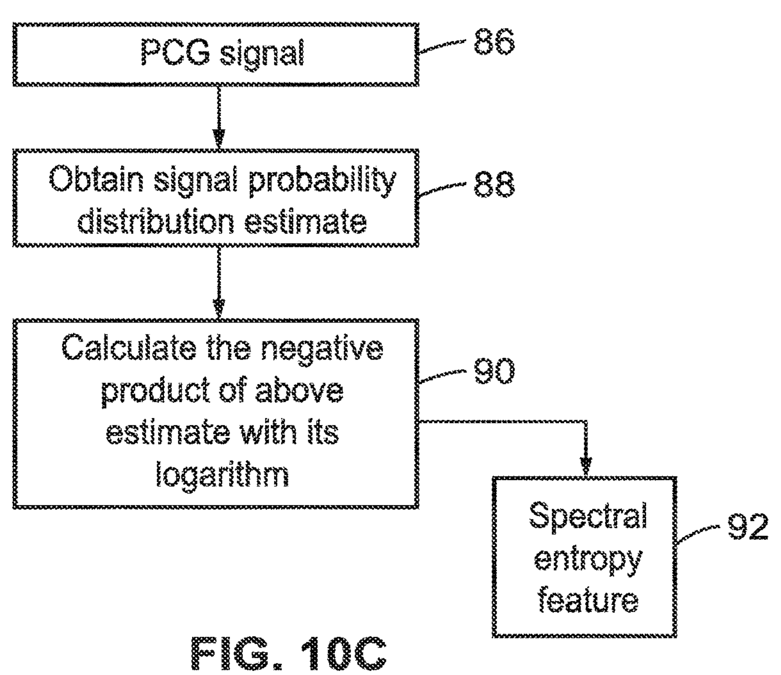
FIG. 10C
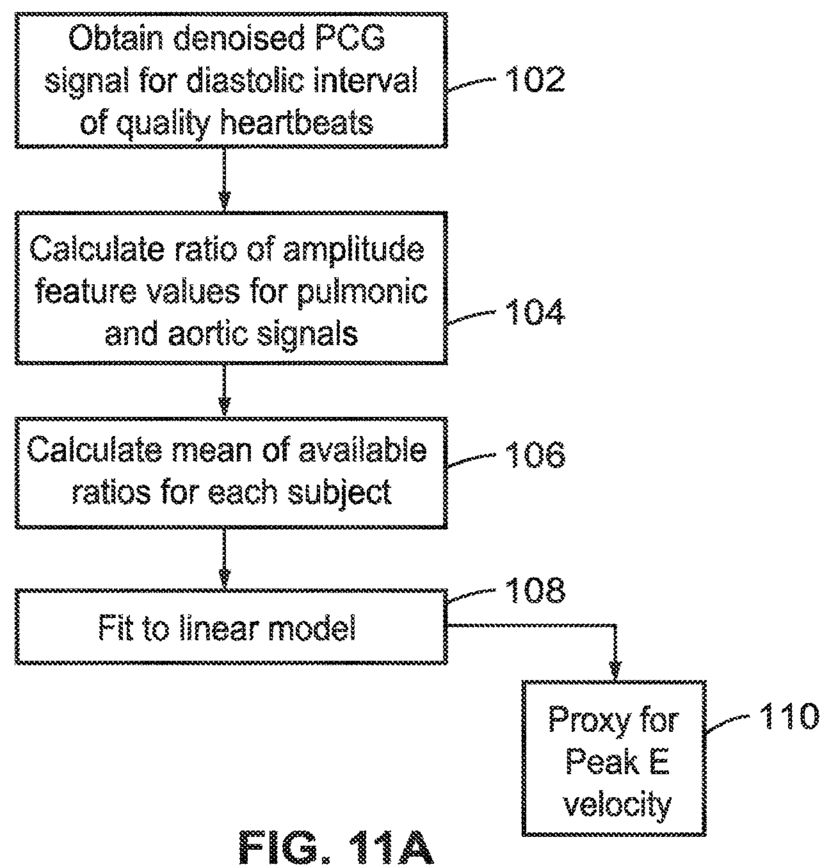
FIG. 11A

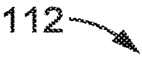
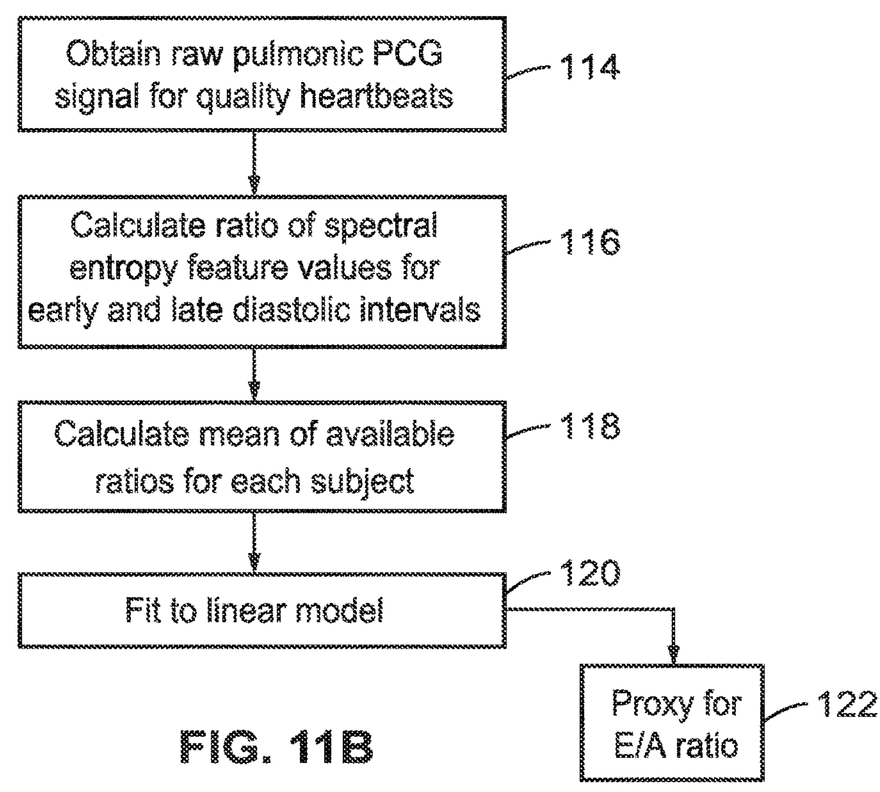
FIG. 11B
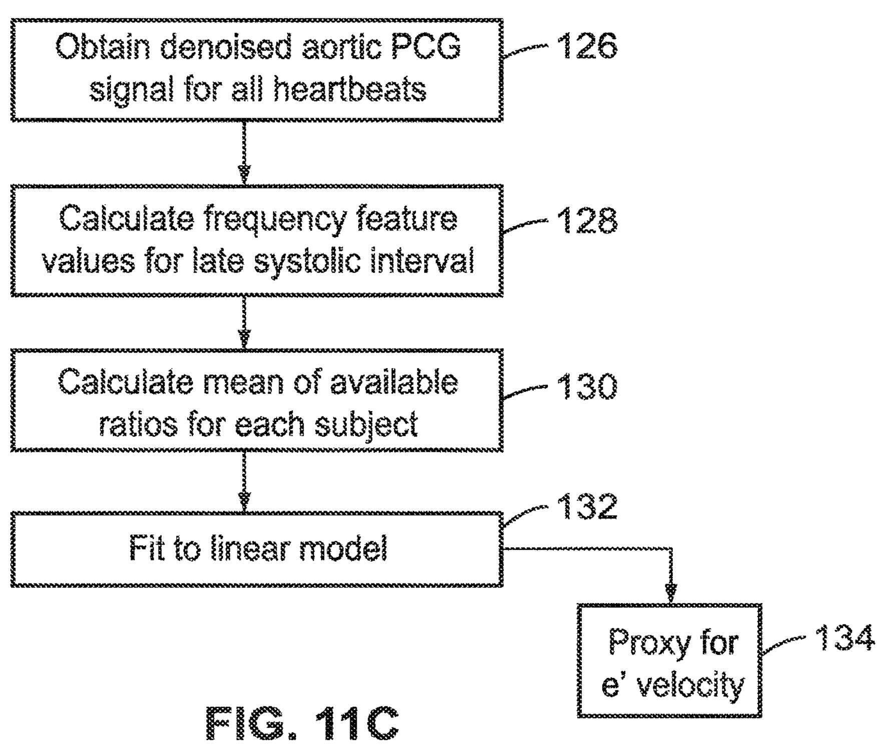
FIG. 11C

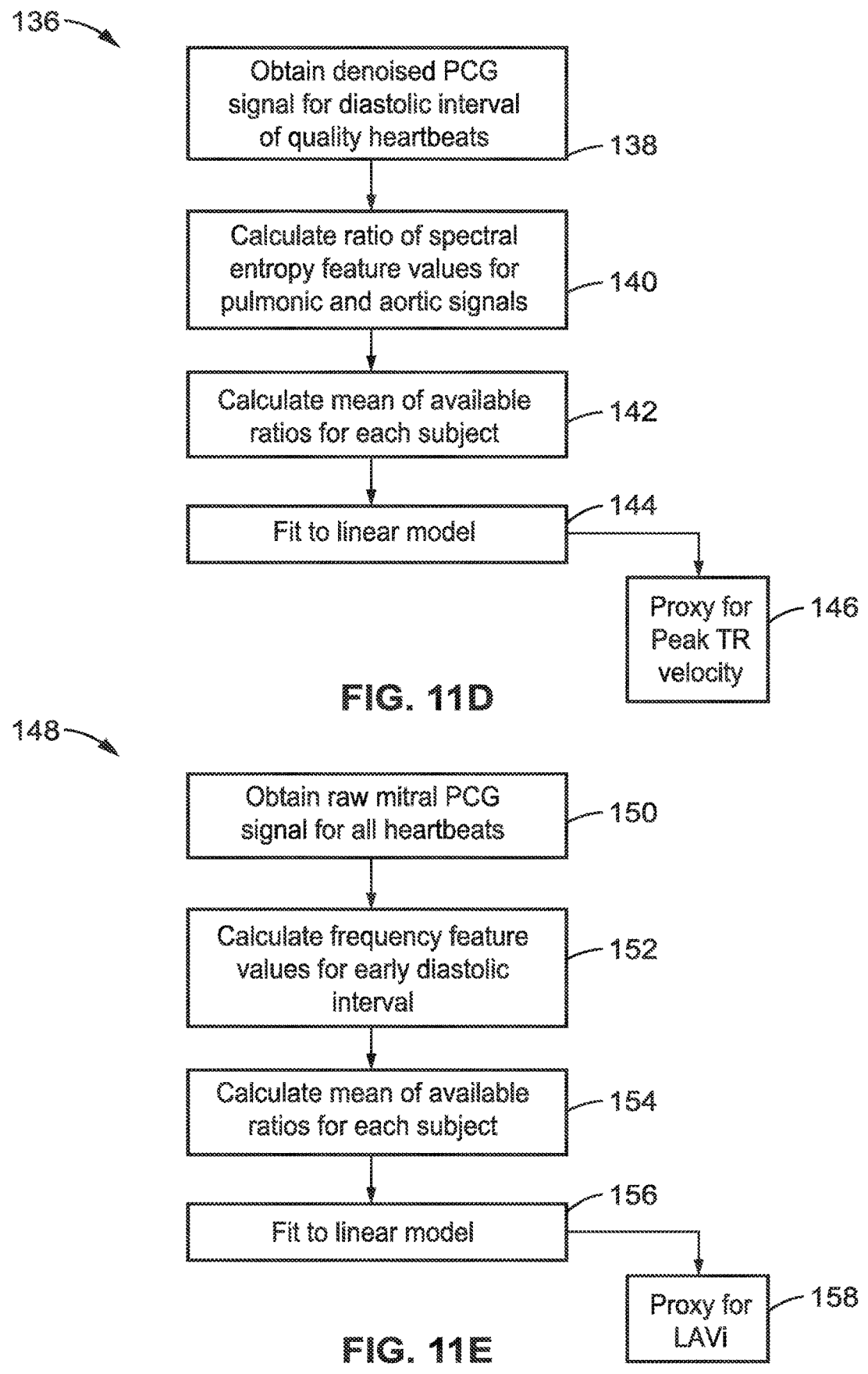

136

Obtain denoised PCG signal for diastolic interval of quality heartbeats — 138

Calculate ratio of spectral entropy feature values for pulmonic and aortic signals — 140

Calculate mean of available ratios for each subject — 142

Fit to linear model — 144

Proxy for Peak TR velocity — 146

Obtain raw mitral PCG signal for all heartbeats — 150

Calculate frequency feature values for early diastolic interval — 152

Calculate mean of available ratios for each subject — 154

Fit to linear model — 156

Proxy for LAVi — 158

FIG. 11E

PHONOCARDIOGRAM (PCG) SIGNAL PROCESSING SYSTEMS AND METHODS FOR DETERMINING CARDIAC TISSUE AND VALVULAR BLOOD FLOW PARAMETERS

CROSS-REFERENCE TO RELATED APPLICATIONS

This application claims priority to, and the benefit of, U.S. provisional patent application Ser. No. 63/332,074 filed on Apr. 18, 2022, incorporated herein by reference in its entirety.

STATEMENT REGARDING FEDERALLY SPONSORED RESEARCH OR DEVELOPMENT

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

This technology pertains generally to systems and methods for providing cardiac assessments and more particularly to non-invasive devices and methods that produce cardiac assessments by computing values of blood flow velocity and tissue motion from heart sounds.

2. Background

The heart is a muscle that pumps blood through the body and is divided into four chambers and has four valves as shown schematically in FIG. 1A and FIG. 1B, respectively. During one cardiac cycle, deoxygenated blood flows from the body into the right side of the heart, routed through the lungs into the left side of the heart and then pumped back out of the heart to the rest of the body as illustrated in FIG. 2.

The pumping efficiency of the heart is conventionally measured by calculating the left ventricular (LV) ejection fraction, which is defined as the fraction of blood in the left ventricle that is pumped out from the heart to the body during each cardiac cycle. This measurement can be represented by the equation:

$$\text{Ejection Fraction} = \frac{\text{Amount of blood pumped out by left ventricle in each cardiac cycle}}{\text{Amount of blood in the left ventricle before pumping begins}}$$

In some cases, the pumping ability of the heart is compromised because the muscles of the left ventricle are unable to relax completely or are too stiff to allow for normal blood filling before pumping, which increases LV filling pressures. This condition is called LV diastolic dysfunction and is one of the biggest reasons for the development of heart failure in humans.

Patients presenting with symptoms of heart failure, such as shortness of breath, fatigue or decreased tolerance to exercise are recommended to undergo an ultrasonic interrogation of the heart, also known as echocardiography. During this imaging technique, a technician visualizes cardiac blood flow and muscle motion and then computes a few parameter values to assess LV dimensions, wall motion, and valvular blood flow patterns. Such echocardiography-based parameters include peak E velocity (the peak velocity of blood flow through the mitral valve during early diastole), E/A ratio (the ratio of early-to-late peak flow velocities through the mitral valve during diastole), e' velocity (the average flow velocity through the mitral valve during early diastole), peak TR velocity (the peak velocity of blood backflow through the tricuspid valve during systole), and LAVi (the maximum volume of left atrium indexed to the body surface area). Cutoff values for each of these parameters are then analyzed to grade the degree of diastolic dysfunction and to estimate LV filling pressures. While a physician can independently analyze these echocardiographic parameters, the accuracy of calculating these parameters depends on the quality of the echocardiographic images and the level of training and experience of the technician. Echocardiography is therefore a resource-intensive tool.

Although non-invasive systems exist that are capable of cardiac assessment, existing systems like ultrasound are not passive or use modalities other than heart sounds such as, for example, ballistocardiography, pressocardiography, or bioimpedance. Existing heart-sound based non-invasive and passive systems claim capabilities for cardiac assessment and abnormal sound detection in general, and may also identify heart afflictions by name, but they do not explicitly claim the capability of assessing cardiac tissue and blood flow parameter computation or provide any evidence for it. In other words, there exist heart sound-based systems that compute blood volume (such as stroke volume or ejection fraction) and blood pressure (such as systolic or diastolic blood pressure, or pulmonary pressures), but none that compute blood flow velocity (such as velocity of blood flow through a heart valve), cardiac tissue motion (such as deflection of valve or heart tissue), or heart chamber size (such as atrial volume).

Accordingly, there is a need for new systems, devices and schemes to allow reliable and accurate measurements of blood flow velocity, cardiac tissue motion and heart chamber dimensions that are non-invasive, low cost and easy to operate.

BRIEF SUMMARY

A non-invasive and automated phonocardiogram (PCG) processing system and method that computes proxy metrics for echocardiographic parameters of cardiac tissue motion and valvular blood flow is provided. The system uses a computer processor and software to receive PCG acoustic signals from one or more sensors and simultaneously receive electrocardiogram (ECG) signals from one or more sensors that are attached to a patient.

The acquired PCG signals are preferably denoised and processed into one or more of temporal features, amplitude features, frequency features, or spectral entropy features for each heartbeat of the same patient.

Then, the processed features are converted into one of several cardiac tissue and valvular blood flow parameter analogues (proxy metrics) based on a set of predetermined conversion equations. In one embodiment, the amplitude features for all heartbeats of the same patient are processed into a proxy metric for the peak velocity of blood flow through the mitral valve of the patient during early diastole (peak E velocity).

In another embodiment, the extracted frequency features for all heartbeats of the same patient are processed into proxy metrics for the average flow velocity through the mitral valve of the patient during early diastole (e' velocity) and the maximum volume of the patient's left atrium indexed to the body surface area (LAVi) of the patient.

In another embodiment the spectral entropy features for all heartbeats of the same subject are processed into a proxy metric for the ratio of early-to-late peak flow velocities through the mitral valve of the patient during diastole (E/A ratio) and the peak velocity of blood backflow through the patient's tricuspid valve during systole (peak TR velocity).

In contrast to existing methods and systems, this technology provides automated methods and systems for cardiac assessment by computing values of blood flow velocity and tissue motion from acquired heart sound (phonocardiogram, PCG) data. The PCG signal acquisition is passive, i.e., it does not involve any application of energy to the body (unlike echocardiography) and is non-invasive. Instead, the methods simply involve recording sounds generated by the heart over a period of time. The methods and systems presented here require signal processing that is beyond a simple mental process and cannot be done using simple computations or observations. These methods and systems are automated and do not require expert supervision. These signal processing methods and systems have been developed using insights from real-world clinical PCG data. The technology rests on the concept of computing these blood velocity and tissue motion parameters from heart sounds and in their utility in assisting the diagnosis and evaluation of heart disease by health care practitioners.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWINGS

The technology described herein will be more fully understood by reference to the following drawings which are for illustrative purposes only:

FIG. 6 is a conceptual diagram of modules and associated module functions of a PCG signal processor according to an embodiment of the technology. The input to the PCG signal processor comprises PCG signals acquired from a subject (upper left), and the output comprises proxies for echocardiographic parameters supplied to the care provider (lower right).

FIG. 7 is a functional block diagram of a non-invasive and automated phonocardiogram (PCG) processing method that computes proxy metrics for echocardiographic parameters such as cardiac tissue motion and valvular blood flow.

FIG. 10C is a functional block diagram of signal processing steps performed by the PCG signal processor for a spectral entropy feature extraction.

FIG. 11A is a functional block diagram of signal processing steps performed by the PCG signal processor for proxy metric computation of peak E velocity.

FIG. 11B is a functional block diagram of signal processing steps performed by the PCG signal processor for proxy metric computation of an E/A ratio.

FIG. 11C is a functional block diagram of signal processing steps performed by the PCG signal processor for proxy metric computation of e' velocity.

FIG. 11D is a functional block diagram of signal processing steps performed by the PCG signal processor for proxy metric computation of peak TR velocity.

FIG. 11E is a functional block diagram of signal processing steps performed by the PCG signal processor for proxy metric computation of LAVi. The processing steps show the type of signal (raw or denoised), source (aortic, pulmonic or mitral), heartbeats (all or quality), signal interval (systolic or diastolic) and feature (amplitude, frequency, or spectral entropy) used.

DETAILED DESCRIPTION

Referring more specifically to the drawings, for illustrative purposes, systems and methods for phonocardiogram (PCG) signal processing that compute proxy metrics for echocardiographic parameters are generally shown. Several embodiments of the technology are described generally in FIG. 1A to FIG. 12B to illustrate the characteristics and functionality of the devices, systems, and methods. It will be appreciated that the methods may vary as to the specific steps and sequence and the systems and apparatus may vary as to structural details without departing from the basic concepts as disclosed herein. The method steps are merely exemplary of the order that these steps may occur. The steps may occur in any order that is desired, such that it still performs the goals of the claimed technology.

Figure 4:
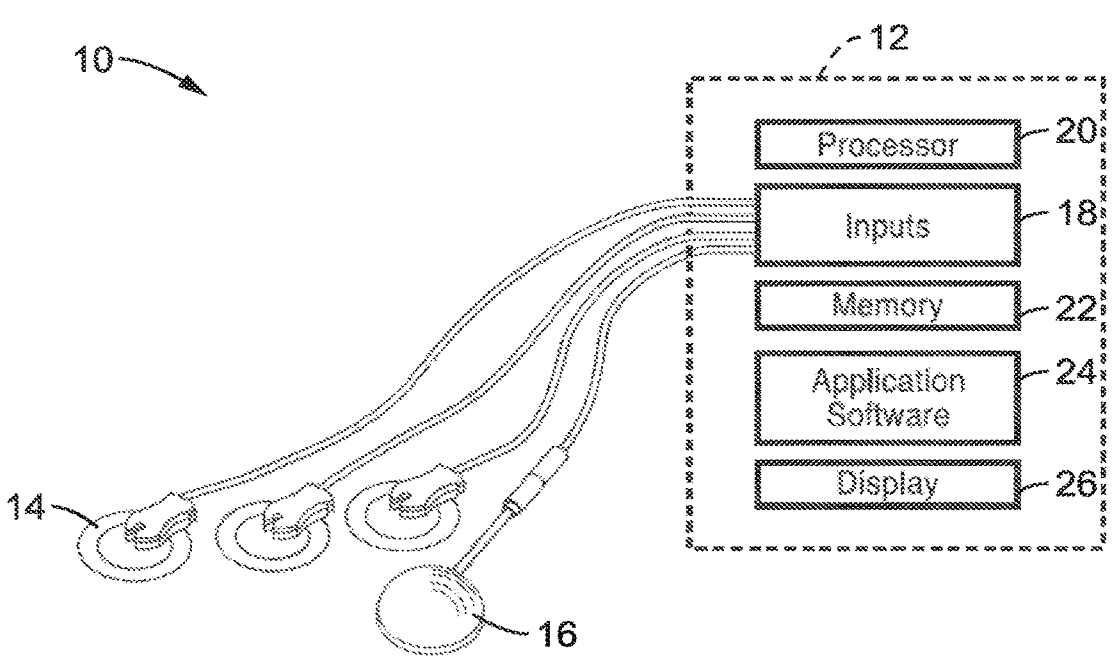
FIG. 4 is a schematic diagram of a signal processor/diagnostic processor architecture according to one embodiment of the technology.

Turning now to FIG. 4, the general structure of one apparatus and system 10 for computing proxy metrics for echocardiographic parameters from phonocardiogram (PCG) signals is shown schematically. The apparatus of system 10 has a control and computing apparatus 12 with one or more electrocardiogram (ECG) sensors 14 producing ECG signals as well as one or more phonocardiogram (PCG) sensors 16 producing PCG signals that are inputs 18 into the apparatus 12. The control/processing apparatus 12 has at least one processor 20, non-transitory memory 22 and application software 24 with programming that processes the ECG and PCG signal inputs 18 as well as extract features, create or apply models and compute proxy metrics as described herein. The apparatus may also have a display 26. The display 26 may be provided for outputting computed analysis or diagnostic results to a health care provider.

In another embodiment, the diagnostic processor may be a separate apparatus or a portion of a the PCG signal processor in which case the application software would also contain instructions for performing the diagnostic processing functions described herein.

Figure 1A:
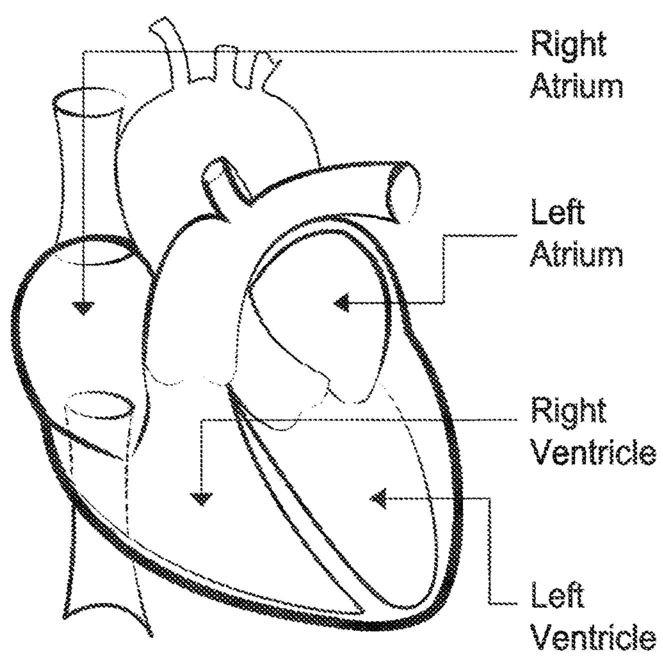
FIG. 1A is a schematic cross-sectional view of the human heart anatomy showing two upper chambers (atria) and two lower chambers (ventricles).
Figure 1B:
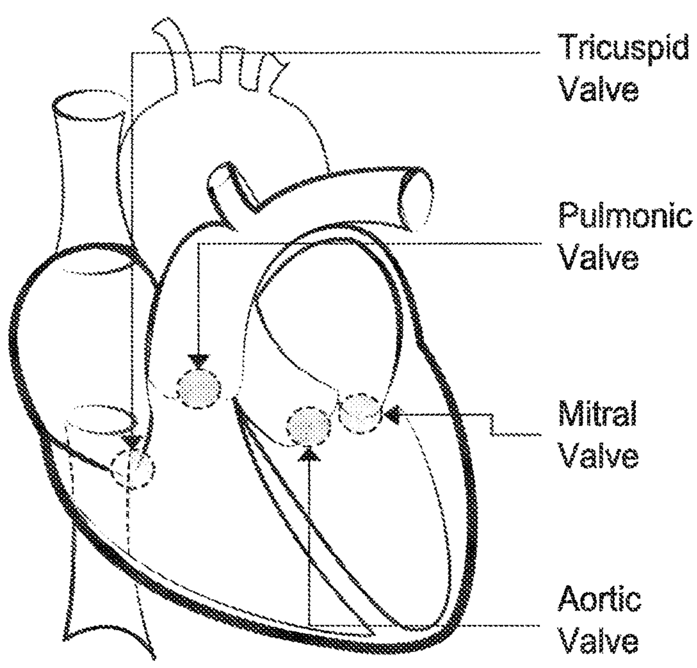
FIG. 1B is a schematic cross-sectional view of the human heart anatomy showing four heart valves.
Figure 2:
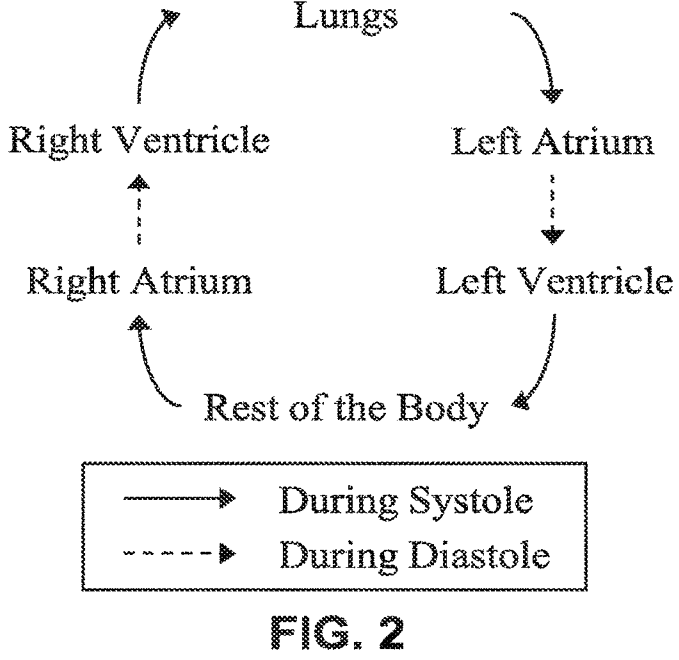
FIG. 2 is a conceptual depiction of the cycle of blood flow through the heart, lungs and organs.
Figure 3:
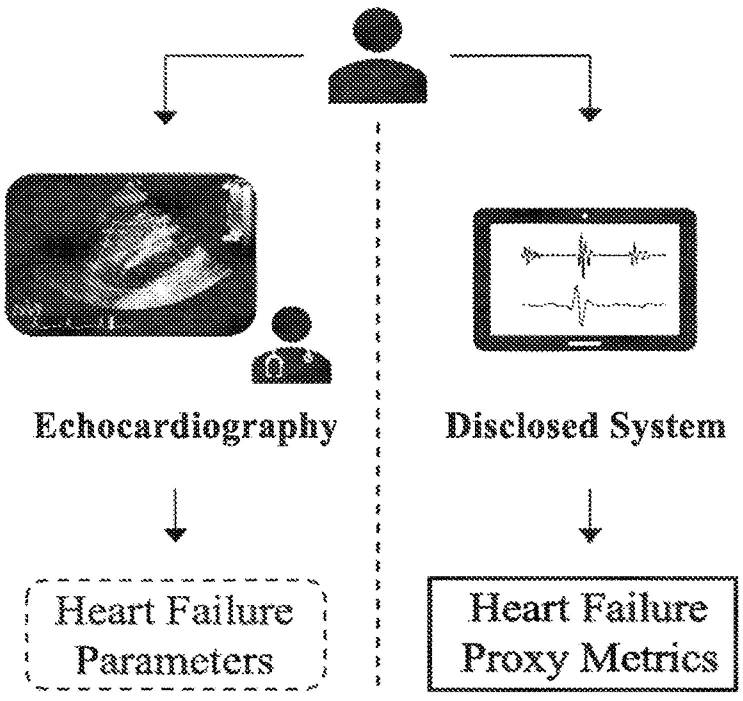
FIG. 3 is a diagram showing the methods and systems according to the technology that uses heart sound data to compute corresponding proxies for echocardiographic parameters for the purpose of evaluating left ventricular function in heart failure.

In one embodiment, a wearable system 10 that uses heart sound (phonocardiogram, PCG) signals to compute PCG-based proxies as equivalents for echocardiographic parameters is provided as illustrated generally in FIG. 3. This computation leverages PCG-signal analysis techniques that determine physiological characteristics of blood flow and muscle motion, and this fully automated system operates without any expert supervision. The physiological characteristics that are used to compute the PCG-based proxy metrics are essentially the same ones that may be otherwise measured by the echocardiographic parameters. This computation involves sophisticated signal processing that cannot be done simply as a mental process, mere observation or with pen and paper. The heart failure screening accuracy of the resulting proxy metric values are comparable to that of echocardiographic parameters, and this system can be used in a clinical care setting for evaluating heart failure patients.

Figure 5:
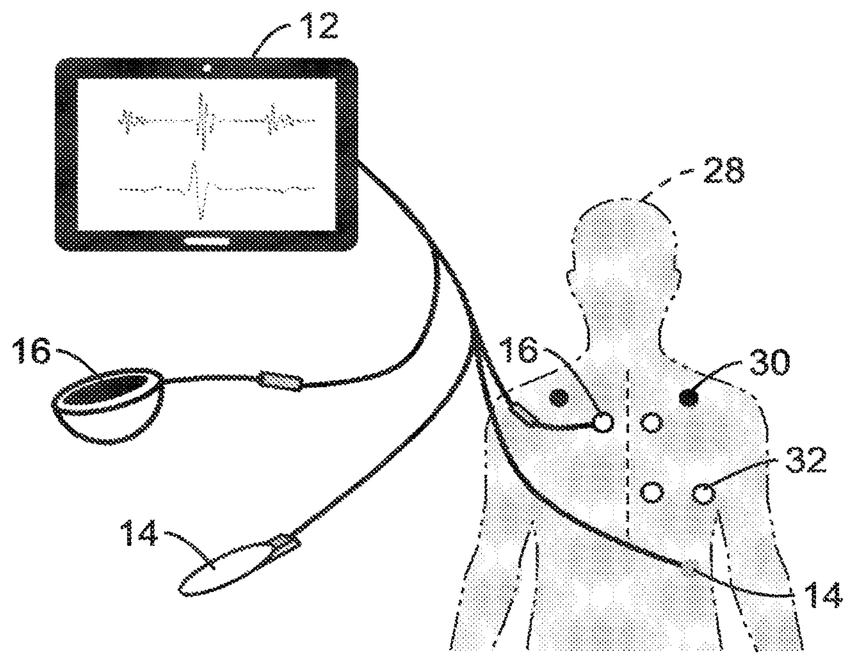
FIG. 5 is a conceptual diagram showing the use of signal acquisition sensors and general placement locations for four acoustic sensors for acquiring PCG signals, and three electrodes for acquiring ECG signals, according to one embodiment of the technology.

In the embodiment shown in FIG. 5, three ECG sensors 14 are placed at specific locations 30 and four PCG acoustic sensors 16 are placed at other locations 32 on the left and right sides of the body 28 of the patient for signal acquisition by the control/processing apparatus 12. Although the number of sensors and locations depicted generally in FIG. 5 are preferred, the number of each sensor type and locations can be varied.

An overview of the sensor signal acquisition and processing steps are set forth generally in FIG. 6 in the context of use. The processing modules and associated module functions of a PCG signal processor 34 from patient acquisition to evaluation of the results by the health practitioner 42 are shown. In this embodiment, the sensor signals from patient 28 are received by the PCG signal processor 34 for processing. At the first module 36, the signals are optionally improved with filtering and noise subtraction. In one embodiment, noise artifacts from speech, motion and other disturbances are removed from the raw PCG signal using band pass filtering and noise subtraction with a spectral noise subtraction algorithm commonly used in speech processing to obtain a PCG signal of qualitatively higher audio fidelity than raw signals.

The denoised signals are then processed with the heartbeat segmentation and quality assurance module 38 in the embodiment shown in FIG. 6. In this module, the start and end times of individual heartbeats in the PCG signal are identified using the ECG signal as reference. The onset of the R wave in each cardiac cycle of the ECG signal can be regarded as the transition point between the end of one heartbeat and start of the next one.

The quality of individual heart beats may also be considered for identification for further processing. A heartbeat may be considered to be a "quality" heartbeat if its signal: (1) has both S1 and S2 successfully identified, (2) has systolic and diastolic intervals free of signal excursions, and (3) has a heartbeat duration within ±20% of median duration for that subject.

The third processing module 40 is for feature extraction and proxy metric computation. In one embodiment, the PCG signal processor processes the PCG signals to transform the signals into three types of features. It is important to note that features are not segments of the PCG signal, but instead represent a distinguishing property obtained from a segment of the PCG signal. As such, feature computation is not a mental process and cannot be done using simple observation or computation, but instead is done using complex signal processing techniques described here. Once the features are extracted, the PCG signal processor then processes those features to transform the features into PCG-based proxy metrics for each of the echocardiographic parameters. These PCG-based proxy metrics are cardiac tissue and valvular blood flow parameter analogues. Proxy metric computation involves extraction of features that characterize physiological phenomena such as cardiac pressure gradients, tissue motion, and blood flow that are otherwise measured by echocardiographic parameters. In one embodiment, the features include an amplitude feature, a frequency feature, and a spectral entropy feature. In one preferred embodiment, the proxy metrics include peak E velocity, e' velocity, LAVi, E/A ratio, and peak TR velocity.

An alternative method 44 for the computation of proxy metrics for echocardiographic parameters from phonocardiogram (PCG) signals is shown in FIG. 7. At block 46, the PCG acoustic signals from one or more acoustic sensors are received or acquired simultaneously with the electrocardiogram (ECG) signals from one or more sensors attached to the subject.

Optionally, the simultaneously received signals can be denoised at block 48 with filters or other signal quality improving approaches. In one embodiment, the PCG signals are denoised by applying a band-pass filter with cutoff frequencies of 25 Hz and 140 Hz, and then applying a spectral noise subtraction algorithm which involves estimating the noise spectrum during brief pauses in heart sound activity. Thereafter, subtracting this estimate from the entire signal's spectrum to obtain a clean heart sound signal at block 48.

In another embodiment, a fourth-order Butterworth low-pass filter is applied to the phonocardiogram signal and the resulting signal envelope is divided into frames. The overall noise spectrum is calculated and subtracted from individual discrete Fourier transforms of signal envelope frames and noise free frames added together to reconstruct the phonocardiogram signal from the entire PCG signal.

Figure 9:
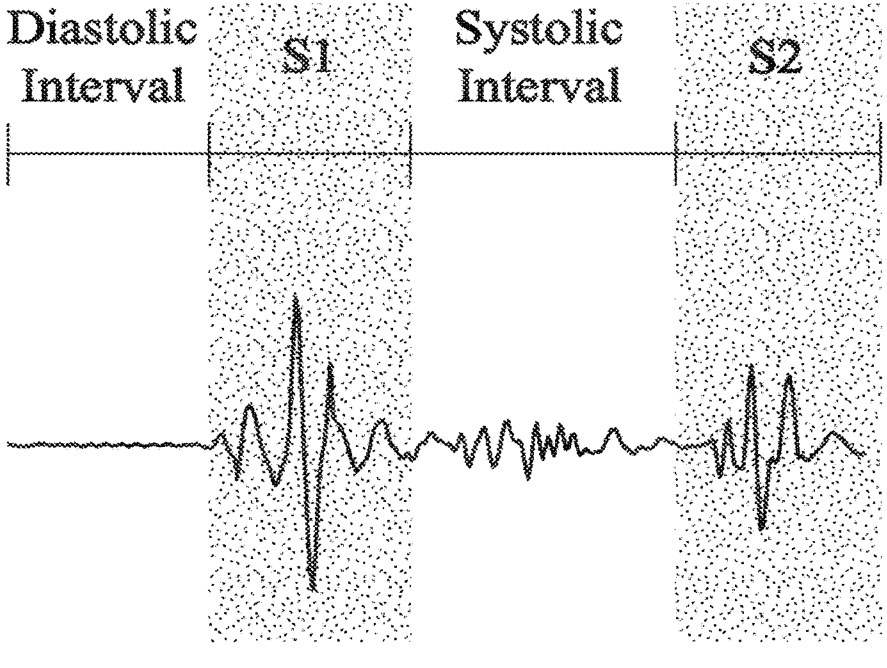
FIG. 9 is an example of a PCG signal for a heartbeat that has been filtered and segmented by the PCG signal processor. The diagram shows the diastolic interval, first heart sound (S1), systolic interval, and second heart sound (S2).

Other denoising approaches may be taken at block 48 to produce a clean heart sound signal. A diagram of a PCG signal for a heartbeat that has been filtered and segmented by the PCG signal processor showing diastolic interval, first heart sound (S1), systolic interval, and second heart sound (S2) is illustrated in FIG. 9.

At block 50 of FIG. 7, raw or denoised PCG signals are processed into one or more of a temporal feature, an amplitude feature, a frequency feature, and/or a spectral entropy feature for each heartbeat of the same subject. The feature extraction process may utilize a case-specific selection of either raw or denoised phonocardiogram signals belonging to either all or exclusively quality heartbeats depending on the underlying physiology being characterized.

Figures 10A, 10B:
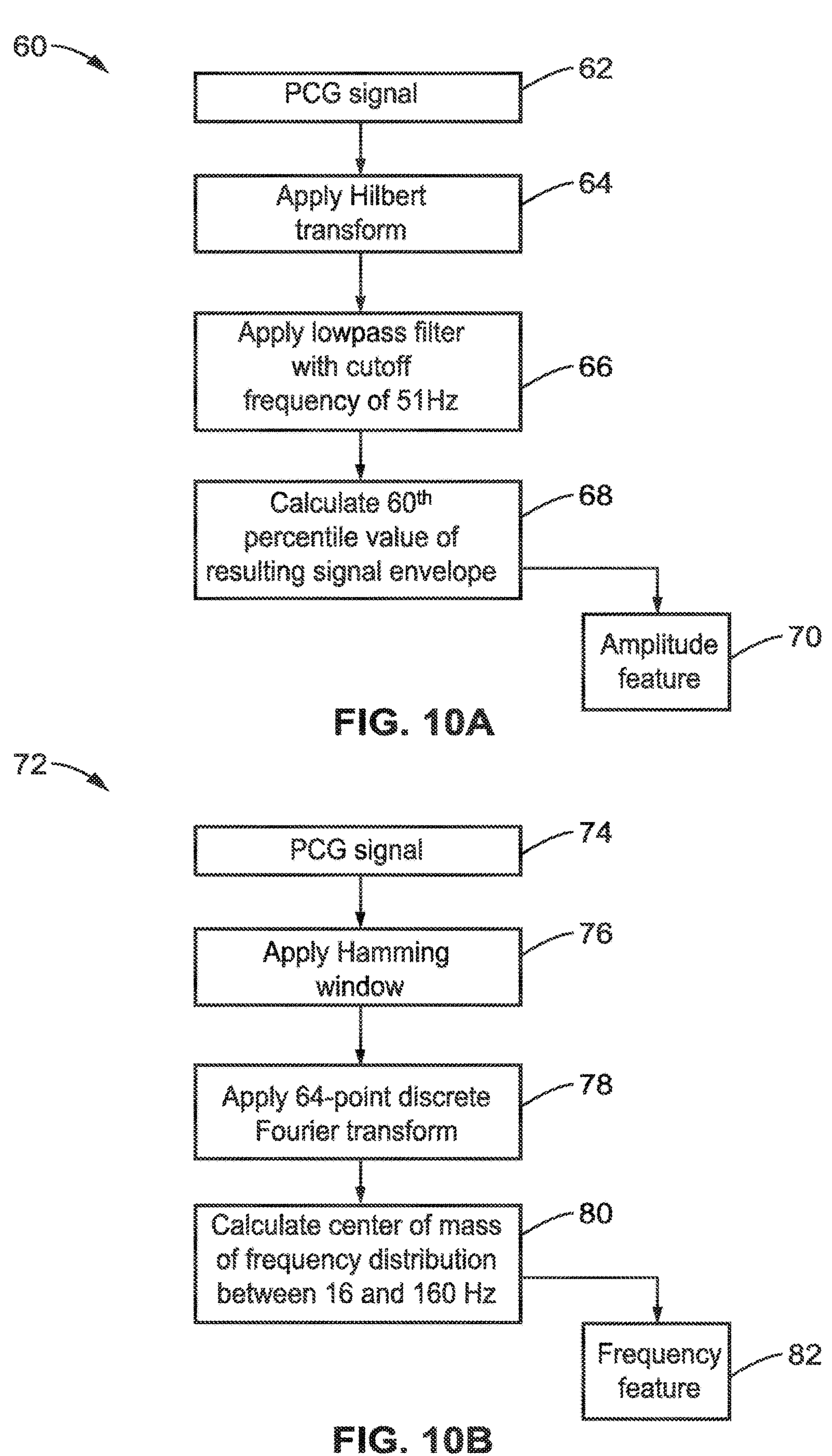
FIG. 10A is a functional block diagram of signal processing steps performed by the PCG signal processor for an amplitude feature extraction.
FIG. 10B is a functional block diagram of signal processing steps performed by the PCG signal processor for a frequency feature extraction.

In one preferred embodiment, the PCG signals are processed into a temporal feature at block 50 of FIG. 7 following the steps shown in FIG. 10A. This process 60 begins with the acquisition of a PCG signal corresponding to one heartbeat at block 62. The acquired signal is processed into an amplitude feature by first applying a Hilbert transform on the PCG signal requiring signal processing in both the time and frequency domains at block 64. At block 66, a low-pass filter with cutoff frequency of 51 Hz is applied, thereby producing a signal envelope. The 60th percentile value of the resulting signal envelope is then calculated for that heartbeat at block 68 to produce the amplitude feature 70.

Referring also to FIG. 10B, one embodiment of a process 72 for producing a frequency feature at block 50 of FIG. 7 is shown. The frequency feature may be processed from a PCG signal acquired at block 74 corresponding to one heartbeat by applying a Hamming window to a segment of the PCG signal at block 76. A 64-point discrete Fourier transform is applied at block 78 and the center of mass of the frequency distribution between 16 Hz and 160 Hz for that heartbeat is calculated at block 80 to produce a frequency feature 82.

In one preferred embodiment, a spectral feature may be calculated using the process 84 shown in FIG. 10C. A PCG signal corresponding to one heartbeat is acquired at block 86 and is processed into a spectral entropy feature by first obtaining a signal distribution probability estimate from the PCG signal at block 88 and calculating a negative product of the signal probability distribution estimate with its logarithm for that heartbeat at block 90 to produce the spectral entropy feature 92.

One or more of these calculated features may then be used to formulate at least one of several proxy metrics as shown in block 52 of FIG. 7. Although specific processes for producing these features are illustrated, other feature extraction processes may be used to obtain the features at block 50 for use in formulating proxy metrics at block 52.

The proxy metrics selected and formulated at block 52 of FIG. 7 are a measure of physiological phenomena that may be compared to a standard. One or more proxy metrics can be formulated at block 52 and the status of different aspects of the heart of the subject patient can be evaluated at block 54 of FIG. 7.

Several transformative PCG-based proxy metrics using the extracted features of FIG. 10A to FIG. 10C are described in FIG. 11A through FIG. 11E to illustrate the methods. The formulated PCG-based proxy metrics for peak E velocity, e' velocity, LAVi, E/A ratio, and peak TR velocity may be output to a diagnostic processor configured for assessing diastolic function and left atrial pressure from the PCG-based proxy metrics at block 54 of FIG. 7.

In one embodiment, a process 100 for deriving a PCG-based proxy metric for echocardiogram-based peak E velocity parameter 110 is determined as shown in FIG. 11A. The proxy metric is obtained by first acquiring denoised PCG signals for diastolic intervals of quality heartbeats at block 102. Ratios of amplitude feature values for pulmonic and aortic signals of each heartbeat are calculated at block 104. Then, the mean of the available ratios across all quality heartbeats for each subject is determined at block 106. The mean is then fitted to a pre-defined linear model using a pre-determined conversion equation at block 108 of FIG. 11A to produce the proxy 110 for the Peak E velocity.

A PCG-based proxy metric for the echocardiogram-based E/A ratio parameter 122 can be determined with the process 112 shown in FIG. 11B. In this embodiment, the proxy metric for the E/A ratio parameter is determined by obtaining raw pulmonic PCG signals for quality heartbeats at block 114. The ratios of the spectral entropy feature values for early and late diastolic intervals of each heartbeat are determined at block 116. The mean of the available ratios across all quality heartbeats for each subject is calculated at block 118. Then, the calculated mean is fitted to a pre-defined linear model using a pre-determined conversion equation at block 120 to produce the E/A ratio proxy metric 122.

An embodiment 124 for processing a proxy metric 134 for an e' velocity parameter is shown in FIG. 11C. Here, the PCG-based proxy metric for the echocardiogram-based e' velocity parameter is determined by obtaining denoised aortic PCG signals for all heartbeats at block 126, calculating frequency feature values for late systolic intervals of each heartbeat at block 128, calculating the mean of available ratios across all heartbeats for each subject at block 130, and then fitting the calculated mean to a pre-defined linear model using a pre-determined conversion equation at block 132 to produce the proxy for e' velocity 134.

A PCG-based proxy metric for the echocardiogram-based peak TR velocity parameter 146 can be determined with the process 136 shown in FIG. 11D. In this embodiment, the PCG-based proxy metric for the echocardiogram-based peak TR velocity parameter is determined by obtaining denoised PCG signals for diastolic intervals of quality heartbeats at block 138. The ratios of spectral entropy feature values for pulmonic and aortic signals of each heartbeat are then calculated at block 140. The mean of available ratios across all quality heartbeats for each subject is calculated at block 142. The calculated mean is then fitted to a pre-defined linear model using a pre-determined conversion equation at block 144 to produce the proxy for peak TR velocity 146.

A PCG-based proxy metric for the echocardiogram-based LAVi parameter 158 can be determined with the process 148 shown in FIG. 11E. In this embodiment, the LAVi parameter is determined by obtaining raw mitral PCG signals for all heartbeats at block 150. The frequency feature values for early diastolic intervals of each heartbeat are then calculated at block 152. At block 154, the mean of available ratios across all heartbeats for each subject is calculated. The calculated mean is fitted to a pre-defined linear model using a pre-determined conversion equation at block 156 to produce the proxy for LAVi 158.

The pre-defined linear models of the processes shown in FIG. 11A to FIG. 11E are preferably generated using training data to determine conversion equations that can be used to compute a proxy metric for any never-seen-before subject, as is the intention of the invention presented here. In other embodiments, signal processing is accompanied with advanced machine learning methods instead of linear regression to provide accurate computation of proxy metrics in these process steps.

In an implementation of this system where a user may select a set of sensors that differ in characteristics from those applied here, it is anticipated that the user must train the system again. This is because it is known that the characteristics of acoustic sensor signals are determined by the specific characteristics of selected sensors. Thus, the linear models and resulting conversion equations must be trained by linear regression with a training dataset obtained with signal acquisition applying the selected sensors on subjects for which corresponding subject condition ground truth has also been obtained.

Accordingly, these PCG-based systems and methods may be used as a part of routine evaluation of patients presenting with symptoms of dyspnea or heart failure and can help them embark on an accelerated path of care. The apparatus and methods are the first of its kind to make non-invasive and passive computations of cardiac tissue and valvular blood flow parameters using heart sound. The end-to-end PCG signal processing, feature extraction, and proxy metric computation algorithms for LV diastolic function evaluation can be operated in a fully automated manner without expert supervision. While the clinical value of the proxy metrics was determined using the 2016 ASE/EACVI algorithm, the proxy metric computation itself was independent of this algorithm and therefore immune to any guideline modification that might be introduced in the future. This demonstrates the utility and potential of the proposed PCG-based system in providing echocardiography-like parameters to the interpreting physician within minutes of signal acquisition in the real-world environment of a hospital or clinic, thereby allowing individuals with heart failure and other cardiac disease to embark on an accelerated path of care.

The technology described herein may be better understood with reference to the accompanying examples, which are intended for purposes of illustration only and should not be construed as in any sense limiting the scope of the technology described herein as defined in the claims appended hereto.

Example 1

In order to demonstrate the operational principles of the technology, a system was designed and validated using a study population of 34 adult inpatients scheduled for right heart catheterization at the Oregon Health and Science University Hospital (Portland, OR). Echocardiographic reports consisting of 2-dimensional and Doppler parameters from a transthoracic examination performed in close proximity to the right heart catheterization were obtained for each subject. Each report included one or more of five parameters based on the quality of the echocardiographic study. See (Table 1). The echocardiographic reports for these se 34 subjects in the subject population constituted the subject condition ground truth data.

The signal acquisition, filtering, heartbeat segmentation and quality assurance features for individuals of this group were also demonstrated and evaluated. During signal acquisition, subjects were lying supine on the catheterization laboratory patient bed.

Phonocardiogram (PCG) signals were acquired at a sample rate of 512 Hz from each subject using four acoustic sensors that were generally placed as illustrated in FIG. 5. Each sensor consisted of an electret microphone housed in an acrylonitrile-butadiene-styrene plastic body with a 0.4 mm-thick black nitrile rubber membrane at one end.

Figure 8:
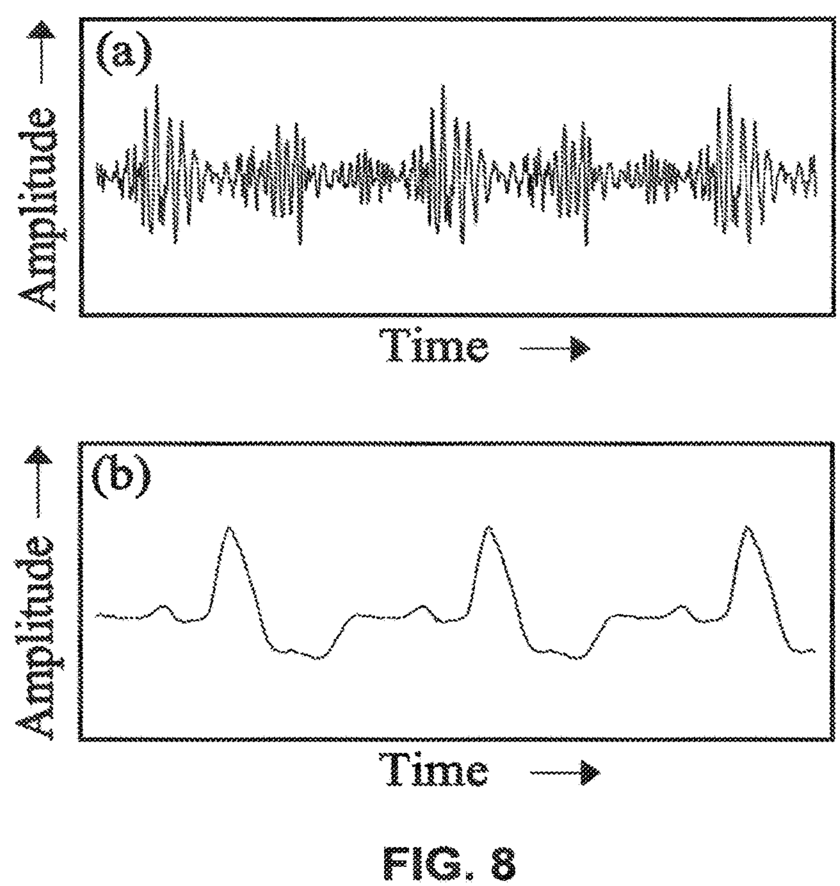
FIG. 8 is an illustration of a PCG signal waveform (top) and an ECG signal waveform (bottom) for three consecutive heartbeats obtained from signal sensors like those shown in FIG. 5.

Sensors were placed membrane side down by the care provider at the four traditional auscultation points on the chest wall-aortic (second intercostal space, right sternal border), pulmonic (second intercostal space, left sternal border), tricuspid (fourth intercostal space, left sternal border) and mitral (fifth intercostal space, left mid-clavicular line). Locations for sensor placement were determined relative to the suprasternal notch and did not require provider intervention. ECG signals were acquired simultaneously at a sample rate of 300 Hz using three ECG electrodes illustrated in FIG. 5. Electrodes were placed proximally on the two upper limbs and (lower left) abdomen. Depending on the catheterization lab schedule, PCG and ECG signal acquisition lasted between 4 and 80 minutes per subject, and these signals were then stored in Matlab (MathWorks, MA) for offline analysis. Example PCG and ECG signal waveforms from consecutive heartbeats are shown in FIG. 8. The PCG and ECG data obtained by this signal acquisition for each of the 34 subjects in the subject population, as described above, together with the subject condition ground truth data described above constituted the training dataset.

A PCG signal processor was designed to perform general PCG signal processing steps of filtering and noise subtraction, heartbeat segmentation and quality assurance, and feature extraction and proxy metric computation as illustrated in FIG. 6 and FIG. 7.

To demonstrate signal filtering and noise subtraction features, the acquired signals from each subject were denoised. Noise artifacts from speech, motion and other disturbances were removed from the raw PCG signal using filtering and noise subtraction to obtain a PCG signal of qualitatively higher audio fidelity than the raw signals. In this illustration, the first step involved applying a band-pass filter with cutoff frequencies of 25 Hz and 140 Hz to retain the maximum amount of heart sound information while removing most low and high-frequency noise artifacts.

The remaining noise artifacts in the mid-frequency range overlapped with the frequency range of heart sound and were instead removed by applying a spectral noise subtraction algorithm commonly used in speech processing. This technique involved estimating the noise spectrum during brief pauses in heart sound activity and then subtracting this estimate from the entire signal's spectrum to obtain a clean heart sound signal. Regions of the PCG signal corresponding to pauses in heart sound activity were identified in the amplitude distribution of the signal envelope on a frame-by-frame basis. For this purpose, a fourth-order Butterworth low-pass filter with a cutoff frequency of 38 Hz was applied to the phonocardiogram signal. The signal envelope obtained as a result was then divided into 93 millisecond-long frames with 31 millisecond (33%) overlaps between adjacent frames. The frame and overlap length were empirically determined to provide the best noise subtraction.

Next, the amplitude distribution for the signal envelope was obtained by arranging the root-mean-square amplitude values of individual frames in increasing order. This amplitude distribution had a roughly bimodal shape with one peak for lower amplitude values corresponding to pauses in heart sound activity and another peak for higher amplitude values corresponding to physiological and pathological heart sounds.

The individual frequency spectra for selected frames in the first peak were calculated using a discrete Fourier transform and these spectra were then averaged to approximate one overall noise spectrum for that PCG signal. This average noise spectrum was then subtracted from individual discrete Fourier transforms of all available signal envelope frames, including those belonging to heart sound activity, and its corresponding time-domain signal was recovered by performing an inverse Fourier transform.

Noise-free signals in each frame were then added together while accounting for the original 33% overlap to reconstruct the phonocardiogram signal for the entire PCG signal. Finally, the same band-pass filter with cutoff frequencies of 25 Hz and 140 Hz was then applied again and the resulting signal was now noise-free.

Heartbeat segmentation and quality assurance features as applied to the denoised or raw signals were also demonstrated. For segmentation, the start and end times of individual heartbeats in the processed PCG signals were identified using the ECG signal as a reference. The onset of the R wave in each cardiac cycle of the ECG signal was regarded as the transition point between the end of one heartbeat and start of the next one. The ECG signal between two consecutive onset points was then identified as one cardiac cycle, and the corresponding PCG signal was therefore identified as one heartbeat. The short-time periodicity of the cardiac cycle, which existed even in severely afflicted cases, was then leveraged to identify the first (S1) and second (S2) heart sounds within each heartbeat. For this, the PCG signal was divided into overlapping frames containing two heartbeats each with one beat of overlap in between consecutive frames, and the signal envelope of each frame was calculated using a low-pass filter with a cutoff frequency of 10 Hz.

A cross correlation was then performed for each frame with a comb function of values zero at all points except $t=0$ and $t=T$ (where T was the time period of the first of the two heartbeats). The location of impulses in this function were expected to be close to the onset of the first S1 peak in the PCG signal frame, and the location of the second S2 peak was T seconds after the first S1 peak. Once both S1 peak locations were known, the start and end time for the S1 heart sounds were determined by searching backwards and forwards form the peak to the time point corresponding to 60% peak height. A similar method was used to identify the second heart sound, however this time the signal envelope was computed using a cutoff frequency of 15 Hz. Previous signal analysis experiments revealed that S2 peaks were found within 0.2T and 0.55T seconds of the S1 peak and therefore the peak in the cross-correlation time series occurring in this time interval after the first most prominent peak informed the location of the S2 peak of the first heartbeat. The start and end times for S2 heart sounds were determined in a similar manner as above.

The identification of the endpoints of S1 and S2 heart sounds allowed for identification of systolic and diastolic intervals in between these heart sounds, as illustrated in FIG. 9. The segmented denoised signal was used to mark corresponding endpoint in the raw PCG signal. Not all heartbeats in the resulting dataset were perfectly segmented and a subset of high-quality heartbeats was therefore created for applications where the entire dataset of heartbeats was not necessary. A heartbeat was considered a quality heartbeat if its signal: (1) had both S1 and S2 successfully identified, (2) has systolic and diastolic intervals free of signal excursions, and (3) had a heartbeat duration within ±20% of median duration for that subject.

To demonstrate the feature extraction process of the methods, the acquired and processed signals of the set of initial subjects were used as the source. The feature extraction process utilized a case-specific selection of either raw or denoised phonocardiogram signals belonging to either all or exclusively quality heartbeats depending on the underlying physiology being characterized.

Example 2

In this Example, the PCG signal processor processed the PCG signals to transform the signals into three types of features including an amplitude feature, a frequency feature, and a spectral entropy feature. These features were then available to formulate proxy metrics including peak E velocity, e' velocity, LAVi, E/A ratio, and peak TR velocity.

The amplitude feature in this Example was generated by applying a Hilbert transform to the selected PCG signal segment and then applying a low-pass filter with cutoff frequency of 51 Hz, thereby producing a signal envelope, as illustrated in process of FIG. 10A. The 60th percentile value of the resulting signal envelope was then calculated and designated as the amplitude feature. This amplitude feature was subsequently used to compute the proxy metric for the peak E velocity parameter. PCG-based proxy metric computation was carried out on a per-heartbeat basis.

The frequency feature was generated by applying a Hamming window to the PCG signal segment and then applying a 64-point discrete Fourier transform following the process of FIG. 10B. The center of mass of the frequency distribution between 16 Hz and 160 Hz was then calculated and designated as the frequency feature. The frequency feature was subsequently used to compute proxy metrics for the e' velocity and LAVi parameters. PCG-based proxy metric computation was carried out on a per-heartbeat basis.

Finally, the spectral entropy feature was generated by obtaining a signal distribution probability estimate from the PCG signal segment and then calculating the negative product of the signal probability distribution estimate with its logarithm as described in the process illustrated in FIG. 10C. The spectral entropy feature was subsequently used to compute proxy metrics for the E/A ratio and peak TR velocity parameters. PCG-based proxy metric computation was carried out on a per-heartbeat basis.

Example 3

To demonstrate the formulation of proxy metrics, a final feature value for each subject was calculated by taking the mean feature value of select heartbeats for that subject. Noise-subtraction, heartbeat segmentation, feature extraction and proxy metric computation proceeded in a fully automated manner. The extracted features directly characterized physiological phenomena otherwise measured by echocardiographic parameters. A summary of features used for each echocardiographic parameter is shown in Table 2 and the processes used are generally described in FIG. 11A through FIG. 11E.

The per-subject feature values were plotted against their echocardiographic parameters, and the proxy metric was estimated for each subject using a linear fit. The linear fit involved first establishing a model of the relationship between the echocardiographic parameter and the PCG feature by computing the constants (slope and intercept) of the linear regression between the two, and then using these calculated constants to estimate a proxy echocardiographic metric for any given PCG feature value. The proxy metric was adjusted by subtracting the linear model's intercept and dividing by its slope, and any proxy values outside physiologically-feasible ranges were truncated accordingly. It will be seen that these pre-defined linear models can be used to compute a proxy metric for any never-seen-before subject and new model derivations may not be needed with every analysis.

The proxy for Peak E velocity was determined by obtaining denoised PCG signals for diastolic intervals of quality heartbeats, calculating ratios of amplitude feature values for pulmonic and aortic signals, calculating the mean of the available ratios for each subject, and fitting the calculated mean to a linear model as illustrated in FIG. 11A.

The Peak E velocity parameter was a measure of peak early diastolic flow velocity at the mitral valve leaflet tips during passive emptying of the left atrium into the left ventricle. The value of this parameter reflected the pressure gradient between the left atrium and left ventricle and was affected by any alterations in the rate of left ventricular relaxation or left atrial pressure. Subjects in the set with high flow velocities showed corresponding high signal amplitudes. The ratio of pulmonic-to-aortic amplitude-based features calculated for the diastolic denoised phonocardiogram signals in high-quality beats was therefore chosen to characterize this trend.

Since the direction of diastolic blood flow was away from the location of aortic and pulmonic auscultation points, lower amplitude-based feature values were seen for high peak E velocity values. The ratio of pulmonic-to-aortic feature values here allowed for the comparison of this trend on the left and right sides of the heart. As a result, greater diastolic amplitude ratios were seen for subjects with larger peak E velocity values, and this ratio was therefore chosen to compute the proxy metric for the peak E velocity parameter.

The proxy for the E/A ratio was determined by obtaining raw pulmonic PCG signals for quality heartbeats, calculating ratios of spectral entropy feature values for early and late diastolic intervals, calculating the mean of the available ratios for each subject, and fitting the calculated mean to a linear model as illustrated in FIG. 11B.

The E/A ratio parameter was a measure of the ratio of early-to-late peak diastolic flow velocities at the mitral valve leaflet tips during the passive and subsequent active emptying of the left atrium into the left ventricle. The value of this parameter was used to identify the state of left ventricular function: normal, impaired relaxation, moderate diastolic dysfunction (pseudoformal filling), or restrictive left ventricular filling (impaired left ventricular compliance).

Diastolic phonocardiogram signal segments associated with left ventricular filling-related muscular contractions were identified using the spectral-entropy based feature. Lower spectral entropy values were seen in late-diastolic signal segments corresponding to active left atrial contractions when compared to early-diastolic signal segments corresponding to passive left atrial emptying. This trend was strongest for raw phonocardiogram signals in high-quality heartbeats acquired at the pulmonic auscultation point. A ratio of early-to-late pulmonic diastolic signal spectral entropy-based features was therefore chosen to compute the proxy metric for the E/A ratio parameter.

The proxy for e' velocity was determined by obtaining denoised aortic PCG signals for all heartbeats, calculating frequency feature values for late systolic intervals, calculating the mean of available ratios for each subject, and fitting the calculated mean to a linear model as illustrated in FIG. 11C.

The e' velocity parameter was a measure of the average early diastolic flow velocity at the mitral valve annulus during passive emptying of the left atrium into the left ventricle. The value of this parameter was seen to be associated with the time constant of left ventricular relaxation. The left ventricular hemodynamic forces responsible for these early-diastolic mitral annulus deflections were indirectly estimated during systole.

While high-frequency vibrations associated with high-velocity blood flow showed corresponding elevated levels of high-frequency signal content, low-frequency vibrations associated with cardiac muscle motion showed corresponding elevated levels of low-frequency signal content. Subjects with high e' velocity values due to larger mitral annulus deflections also showed greater muscle motion-related low frequency content during systole. This phenomenon was characterized by calculating the frequency-based feature for the denoised end-systolic phonocardiogram signals in all heartbeats acquired at the aortic auscultation point. This feature was therefore chosen to compute the proxy metric for the e' velocity parameter.

The proxy for peak TR velocity was determined by obtaining denoised PCG signals for diastolic intervals of quality heartbeats, calculating ratios of spectral entropy feature values for pulmonic and aortic signals, calculating the mean of available ratios for each subject, and fitting the calculated mean to a linear model as shown in FIG. 11D.

The Peak TR velocity parameter was a measure of the peak regurgitant systolic jet velocity at the tricuspid valve during right ventricular contraction. The value of this parameter provided an indirect measure of the pulmonary artery systolic pressure which was seen to be directly correlated to left atrial pressure. Subjects with greater peak TR velocity values and therefore higher pulmonary artery pressures have been observed to show organized heart sound patterns in phonocardiogram signals collected at the pulmonic auscultation point. These patterns were characterized by calculating the ratio of the spectral entropy-based feature for the diastolic interval phonocardiogram signal acquired at the pulmonic and aortic auscultation points.

Lower spectral entropy values were seen at the pulmonic auscultation point for subjects with greater peak TR velocity values. This trend was strongest for denoised phonocardiogram signals in high-quality heartbeats, and this ratio was therefore chosen to compute the proxy metric for the peak TR velocity parameter.

The proxy for LAVi was determined by obtaining raw mitral PCG signals for all heartbeats, calculating frequency feature values for early diastolic intervals, calculating the mean of available ratios for each subject, and fitting the calculated mean to a linear model as illustrated in FIG. 11E.

The LAVi parameter was a measure of the maximum left atrial volume indexed to body surface area. The value of this parameter reflected the cumulative effects of increased left atrial pressures over time. Subjects with greater LAVi values and therefore larger left atria showed greater muscle-motion related low-frequency signal content during left ventricular filling in early diastole. This trend was characterized by calculating the frequency-based feature for the early diastolic interval phonocardiogram signal acquired at the mitral auscultation point and was strongest for raw phonocardiogram signals in all heartbeats. This feature was therefore chosen to compute the proxy metric for the LAVi parameter.

Proxy metrics could not be calculated for all subjects due to occasional signal quality deficiencies associated with measurement in the noisy catheterization laboratory environment. Peak E velocity and peak TR velocity proxies were unavailable for 6 subjects each, e' velocity for three subjects, and LAVi for one subject.

Example 4

A comparison of the proxy metric results with existing echocardiography and standards was conducted to verify the diagnostic accuracy of the apparatus and methods. The clinical value of proxy metrics was evaluated using a diagnostic processor employing a customized diagnostic algorithm based on the algorithm described in the joint recommendations of the American Society of Echocardiography (ASE) and the European Association of Cardiovascular Imaging (EACVI) in 2016.

Figure 12A:
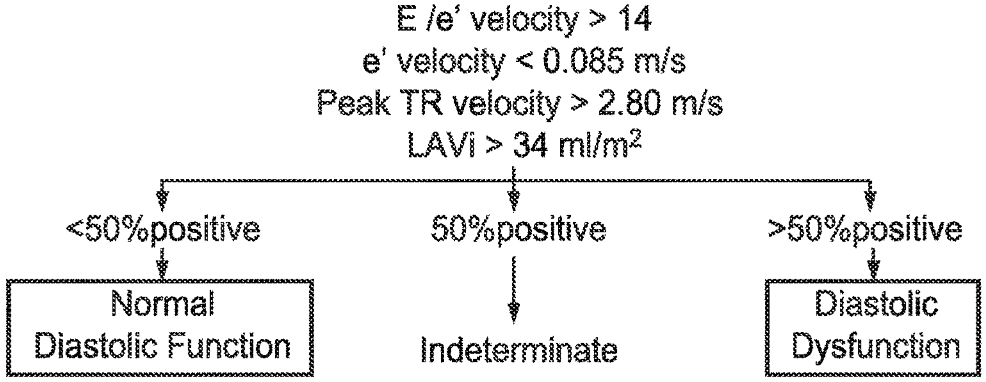
FIG. 12A is a conceptual diagram of a diagnostic standard described in the joint recommendations of the American Society of Echocardiography (ASE) and the European Association of Cardiovascular Imaging (EACVI) in 2016 for evaluation of LV diastolic function.
Figure 12B:
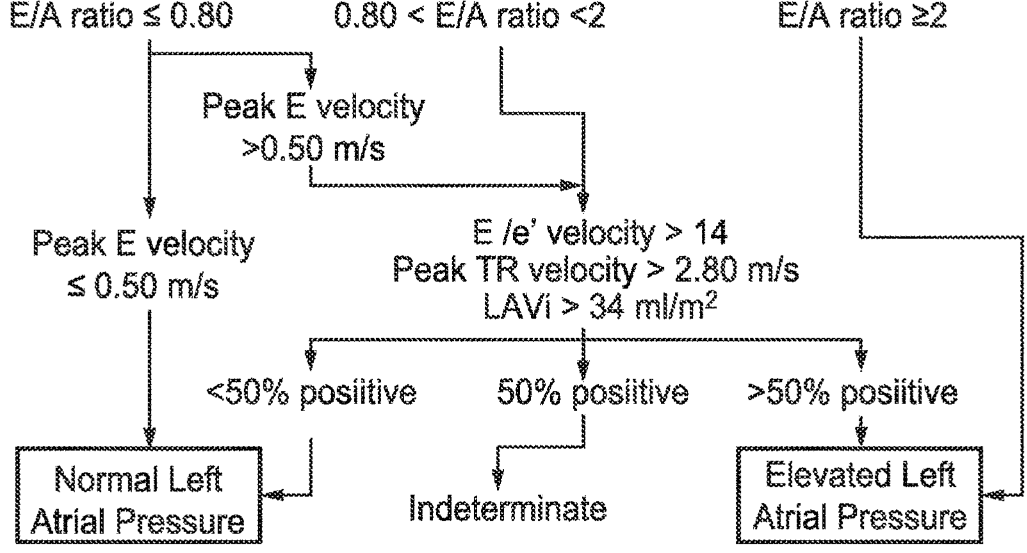
FIG. 12B is a conceptual diagram of a diagnostic standard for estimation of mean left atrial pressure as a reliable approximation of LV filling pressure from the same source. Cutoff value for "average" e' velocity was chosen as the mean of those for "septal" and "lateral" e' velocities.

The diagram shown in FIG. 12A represents elements of an algorithm for the assessment of left ventricular diastolic dysfunction in patients with normal left ventricular ejection fraction (LVEF). This algorithm was customized to use peak E velocity, e' velocity, peak TR velocity and LAVi to identify subjects with LV diastolic dysfunction in the presence of normal LV ejection fraction values. The standard parameters that were used are shown in FIG. 12A. Referring also to FIG. 12B, the second part of the algorithm was customized to use the above 4 parameters along with E/A ratio to estimate the mean left atrial pressure (as an indirect measure of LV filling pressure) for subjects with reduced ejection fraction values or those with normal ejection fraction values in presence of underlying myocardial disease. The parameters used are shown in the diagram of FIG. 12B.

The goal of this Example was to compare PCG-based proxy metrics with echocardiographic parameters for LV diastolic function assessment using this 2016 ASE/EACVI algorithm. Ground truth diastolic dysfunction and left atrial pressure evaluations were obtained for each subject using their echocardiographic parameters irrespective of their ejection fraction value.

Proxy metrics identified LV diastolic dysfunction in 29 subjects with 87.5% accuracy, and elevated LV filling pressures in 17 subjects with 75% accuracy. These numbers were closely in line with those reported in reference studies comparing diagnostic accuracy of echocardiographic parameters with gold-standard invasive-catheter pressure measurements. Potential sources of error in proxy metric computation were that PCG signals were not recorded concurrently with echocardiographic parameters or due to occasional signal quality deficiencies during measurement in the noisy catheterization laboratory environment.

From the description herein, it will be appreciated that the present disclosure encompasses multiple embodiments which include, but are not limited to, the following:

A system for computing proxy metrics of echocardiographic parameters, comprising: (a) one or more phonocardiogram (PCG) sensors; (b) one or more electrocardiogram (ECG) sensors; (c) a computer processor; and (d) a non-transitory memory storing instructions executable by the computer processor; (e) wherein the instructions, when executed by the processor, cause the processor to perform steps comprising: (i) receiving PCG acoustic signals from one or more PCG sensors attached to a subject; (ii) receiving simultaneously electrocardiogram (ECG) signals from one or more ECG sensors attached to the subject; (iii) optionally denoising the received PCG acoustic signals; (iv) processing the PCG signals into one or more of temporal features, amplitude features, frequency features, or spectral entropy features for each heartbeat of the subject; and (v) converting the processed features into one or more proxy metrics of cardiac tissue and valvular blood flow parameters with a set of predetermined conversion equations.

The system of any preceding or following implementation, wherein denoising of the received PCG acoustic signals comprises: applying a band-pass filter with cutoff frequencies of 25 Hz and 140 Hz to the PCG acoustic signals; estimating a spectral noise spectrum during brief pauses in heart sound activity; and subtracting the estimate from a spectrum of the whole signal to obtain a clean heart sound signal.

The system of any preceding or following implementation, wherein the instructions when, executed by the processor, further perform steps comprising: identifying start and end times of individual heartbeats in PCG signals using ECG signals as a reference; identifying first (S1) and second (S2) heart sounds, and diastolic and systolic intervals within each identified heartbeat; and assessing whether a heartbeat qualifies as a quality heartbeat by determining whether both S1 and S2 have been successfully identified, determining whether systolic and diastolic intervals are free of signal excursions, and determining whether the heartbeat duration is within ±20% of median duration for the subject.

The system of any preceding or following implementation, wherein the amplitude feature processing comprises applying a Hilbert transform on the PCG signal with signal processing in both the time and frequency domains; applying a low-pass filter with cutoff frequency of 51 Hz, thereby producing a signal envelope, and calculating the 60th percentile value of the resulting signal envelope for that heartbeat.

The system of any preceding or following implementation, wherein the frequency feature processing comprises isolating a PCG signal corresponding to one heartbeat; applying a Hamming window to a segment of the PCG signal; applying a 64-point discrete Fourier transform, and calculating a center of mass of a frequency distribution between 16 Hz and 160 Hz for the heartbeat.

The system of any preceding or following implementation, wherein the spectral entropy frequency feature processing comprises isolating a PCG signal corresponding to one heartbeat; obtaining a signal distribution probability estimate from the PCG signal; and calculating a negative product of the signal probability distribution estimate with its logarithm for that heartbeat.

The system of any preceding or following implementation, wherein each conversion equation is generated using linear regression applied to a training dataset of subject condition ground truth data and sensor signal data obtained for a subject population.

The system of any preceding or following implementation, wherein the calculation of a PCG-based proxy metric for echocardiogram-based peak E velocity parameter comprises: obtaining denoised PCG signals for diastolic intervals; identifying quality heartbeats; calculating ratios of amplitude feature values for pulmonic and aortic signals of each heartbeat; calculating a mean of available ratios across all quality heartbeats for each subject; and fitting the calculated mean to a pre-defined linear model using a predetermined conversion equation.

The system of any preceding or following implementation, wherein the calculation of a PCG-based proxy metric for the echocardiogram-based E/A ratio parameter comprises obtaining raw pulmonic PCG signals for quality heartbeats; calculating ratios of spectral entropy feature values for early and late diastolic intervals of each heartbeat; calculating the mean of the available ratios across all quality heartbeats for each subject; and fitting the calculated mean to a pre-defined linear model using a pre-determined conversion equation.

The system of any preceding or following implementation, wherein the calculation of a PCG-based proxy metric for the echocardiogram-based e' velocity parameter comprises obtaining denoised aortic PCG signals for all heartbeats; calculating frequency feature values for late systolic intervals of each heartbeat; calculating a mean of available ratios across all heartbeats for each subject; and fitting the calculated mean to a pre-defined linear model using a pre-determined conversion equation.

The system of any preceding or following implementation, wherein the calculation of a PCG-based proxy metric for the echocardiogram-based peak TR velocity parameter comprises obtaining denoised PCG signals for diastolic intervals of quality heartbeats; calculating ratios of spectral entropy feature values for pulmonic and aortic signals of each heartbeat; calculating the mean of available ratios across all quality heartbeats for each subject; and fitting the calculated mean to a pre-defined linear model using a pre-determined conversion equation.

The system of any preceding or following implementation, wherein the calculation of a PCG-based proxy metric for the echocardiography-based LAVi parameter comprises obtaining raw mitral PCG signals for all heartbeats; calculating frequency feature values for early diastolic intervals of each heartbeat; calculating the mean of available ratios across all heartbeats for each subject; and fitting the calculated mean to a pre-defined linear model using a pre-determined conversion equation.

The system of any preceding or following implementation, wherein the PCG-based proxy metrics for peak E velocity, e' velocity, LAVi, E/A ratio, and peak TR velocity are output to a diagnostic processor configured for assessing diastolic function and left atrial pressure from the PCG-based proxy metrics.

A method for computing proxy metrics for echocardiographic parameters, the method comprising: (a) receiving PCG acoustic signals from one or more sensors attached to a subject; (b) receiving simultaneously electrocardiogram (ECG) signals from one or more sensors attached to the subject; (c) processing the denoised PCG signals into one or more of temporal features, amplitude features, frequency features, or spectral entropy features for each heartbeat of the same subject; (d) converting the extracted features into a plurality of cardiac tissue and valvular blood flow parameter analogues (proxy metrics) based on a set of predetermined conversion equations, the conversions comprising; (i) processing the amplitude features for all heartbeats of the same subject into a proxy metric for the peak velocity of blood flow through the subject's mitral valve during early diastole (peak E velocity); (ii) processing the frequency features for all heartbeats of the same subject into proxy metrics for the average flow velocity through the subject's mitral valve during early diastole (e' velocity) and the maximum volume of the subject's left atrium indexed to the subject's body surface area (LAVi); and (iii) processing the spectral entropy features for all heartbeats of the same subject into a proxy metric for the ratio of early-to-late peak flow velocities through the subject's mitral valve during diastole (E/A ratio) and the peak velocity of blood backflow through the subject's tricuspid valve during systole (peak TR velocity).

The method of any preceding or following implementation, further comprising denoising of the received PCG acoustic signals, the denoising comprising applying a band-pass filter with cutoff frequencies of 25 Hz and 140 Hz to the PCG acoustic signals; estimating a spectral noise spectrum during brief pauses in heart sound activity; and subtracting the estimate from a spectrum of the whole signal to obtain a clean heart sound signal.

The method of any preceding or following implementation, further comprising identifying start and end times of individual heartbeats in PCG signals using ECG signals as a reference; identifying first (S1) and second (S2) heart sounds, and diastolic and systolic intervals within each identified heartbeat; and assessing whether a heartbeat qualifies as a quality heartbeat by determining whether both S1 and S2 have been successfully identified, determining whether systolic and diastolic intervals are free of signal excursions, and determining whether the heartbeat duration is within ±20% of median duration for the subject.

The method of any preceding or following implementation, wherein the amplitude feature processing comprises applying a Hilbert transform on the PCG signal with signal processing in both the time and frequency domains; applying a low-pass filter with cutoff frequency of 51 Hz, thereby producing a signal envelope, and calculating the 60th percentile value of the resulting signal envelope for that heartbeat.

The method of any preceding or following implementation, wherein the frequency feature processing comprises isolating a PCG signal corresponding to one heartbeat; applying a Hamming window to a segment of the PCG signal; applying a 64-point discrete Fourier transform, and calculating a center of mass of a frequency distribution between 16 Hz and 160 Hz for the heartbeat.

The method of any preceding or following implementation, wherein the spectral entropy frequency feature processing comprises isolating a PCG signal corresponding to one heartbeat; obtaining a signal distribution probability estimate from the PCG signal; and calculating a negative product of the signal probability distribution estimate with its logarithm for that heartbeat.

The method of any preceding or following implementation, wherein the calculation of a PCG-based proxy metric for echocardiogram-based peak E velocity parameter comprises obtaining denoised PCG signals for diastolic intervals; identifying quality heartbeats; calculating ratios of amplitude feature values for pulmonic and aortic signals of each heartbeat; calculating a mean of available ratios across all quality heartbeats for each subject; and fitting the calculated mean to a pre-defined linear model using a pre-determined conversion equation.

The method of any preceding or following implementation, wherein the calculation of a PCG-based proxy metric for the echocardiogram-based E/A ratio parameter comprises obtaining raw pulmonic PCG signals for quality heartbeats; calculating ratios of spectral entropy feature values for early and late diastolic intervals of each heartbeat; calculating the mean of the available ratios across all quality heartbeats for each subject; and fitting the calculated mean to a pre-defined linear model using a pre-determined conversion equation.

The method of any preceding or following implementation, wherein the calculation of a PCG-based proxy metric for the echocardiogram-based e' velocity parameter comprises obtaining denoised aortic PCG signals for all heartbeats; calculating frequency feature values for late systolic intervals of each heartbeat; calculating a mean of available ratios across all heartbeats for each subject; and fitting the calculated mean to a pre-defined linear model using a pre-determined conversion equation.

The method of any preceding or following implementation, wherein the calculation of a PCG-based proxy metric for the echocardiogram-based peak TR velocity parameter comprises obtaining denoised PCG signals for diastolic intervals of quality heartbeats; calculating ratios of spectral entropy feature values for pulmonic and aortic signals of each heartbeat; calculating the mean of available ratios across all quality heartbeats for each subject; and fitting the calculated mean to a pre-defined linear model using a pre-determined conversion equation.

The method of any preceding or following implementation, wherein the calculation of a PCG-based proxy metric for the echocardiography-based LAVi parameter comprises obtaining raw mitral PCG signals for all heartbeats; calculating frequency feature values for early diastolic intervals of each heartbeat; calculating the mean of available ratios across all heartbeats for each subject; and fitting the calculated mean to a pre-defined linear model using a pre-determined conversion equation.

As used herein, the term "implementation" is intended to include, without limitation, embodiments, examples, or other forms of practicing the technology described herein.

As used herein, the singular terms "a," "an," and "the" may include plural referents unless the context clearly dictates otherwise. Reference to an object in the singular is not intended to mean "one and only one" unless explicitly so stated, but rather "one or more."

Phrasing constructs, such as "A, B and/or C", within the present disclosure describe where either A, B, or C can be present, or any combination of items A, B and C. Phrasing constructs indicating, such as "at least one of" followed by listing a group of elements, indicates that at least one of these group elements is present, which includes any possible combination of the listed elements as applicable.

References in this disclosure referring to "an embodiment", "at least one embodiment" or similar embodiment wording indicates that a particular feature, structure, or characteristic described in connection with a described embodiment is included in at least one embodiment of the present disclosure. Thus, these various embodiment phrases are not necessarily all referring to the same embodiment, or to a specific embodiment which differs from all the other embodiments being described. The embodiment phrasing should be construed to mean that the particular features, structures, or characteristics of a given embodiment may be combined in any suitable manner in one or more embodiments of the disclosed apparatus, system or method.

As used herein, the term "set" refers to a collection of one or more objects. Thus, for example, a set of objects can include a single object or multiple objects.

Relational terms such as first and second, top and bottom, and the like may be used solely to distinguish one entity or action from another entity or action without necessarily requiring or implying any actual such relationship or order between such entities or actions.

The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element.

As used herein, the terms "approximately", "approximate", "substantially", "essentially", and "about", or any other version thereof, are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

The term "coupled" as used herein is defined as connected, although not necessarily directly and not necessarily mechanically. A device or structure that is "configured" in a certain way is configured in at least that way, but may also be configured in ways that are not listed.

Benefits, advantages, solutions to problems, and any element(s) that may cause any benefit, advantage, or solution to occur or become more pronounced are not to be construed as a critical, required, or essential features or elements of the technology describes herein or any or all the claims.

In addition, in the foregoing disclosure various features may grouped together in various embodiments for the purpose of streamlining the disclosure. This method of disclosure is not to be interpreted as reflecting an intention that the claimed embodiments require more features than are expressly recited in each claim. Inventive subject matter can lie in less than all features of a single disclosed embodiment.

The abstract of the disclosure is provided to allow the reader to quickly ascertain the nature of the technical disclosure. It is submitted with the understanding that it will not be used to interpret or limit the scope or meaning of the claims.

It will be appreciated that the practice of some jurisdictions may require deletion of one or more portions of the disclosure after that application is filed. Accordingly the reader should consult the application as filed for the original content of the disclosure. Any deletion of content of the disclosure should not be construed as a disclaimer, forfeiture or dedication to the public of any subject matter of the application as originally filed.

The following claims are hereby incorporated into the disclosure, with each claim standing on its own as a separately claimed subject matter.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

Summary of Parameters available in Echocardiographic Reports

| Parameter | Description | Number of Subjects this Parameter was Available for |
|---|---|---|
| Peak E velocity | The peak velocity of blood flow through the mitral valve during early diastole | 26 |
| E/A ratio | The ratio of early-to-late peak flow velocities through the mitral valve during diastole | 18 |
| e' velocity | The average flow velocity through the mitral valve during early diastole | 23 |
| Peak TR velocity | The peak velocity of blood backflow through the tricuspid valve during systole | 22 |
| LAVi | The maximum volume of left atrium indexed to the body surface area | 25 |

TABLE 2

Summary of Features used to Compute Proxies for Echocardiographic Parameters

| Parameter | Feature used to Compute Proxy Metric |
|---|---|
| Peak E velocity | Ratio of pulmonic-to-aortic diastolic amplitude for denoised signal in quality heartbeats |
| E/A ratio | Ratio of early-to-late pulmonic diastolic spectral entropy for raw signal in quality heartbeats |
| e' velocity | Aortic late-systolic frequency center of mass for denoised signal in all heartbeats |
| Peak TR velocity | Ratio of pulmonic-to-aortic diastolic interval spectral entropy for denoised signal in quality heartbeats |
| LAVi | Mitral early-diastolic frequency center of mass for raw signal in all heartbeats |

What is claimed is:

1. A system for computing proxy metrics of echocardiographic parameters, comprising:
   - (a) one or more phonocardiogram (PCG) sensors;
   - (b) one or more electrocardiogram (ECG) sensors;
   - (c) a computer processor; and
   - (d) a non-transitory memory storing instructions executable by the computer processor;
   - (e) wherein the instructions, when executed by the processor, cause the processor to perform steps comprising:
     - (i) receiving PCG acoustic signals from one or more PCG sensors attached to a subject;
     - (ii) receiving simultaneously electrocardiogram (ECG) signals from one or more ECG sensors attached to the subject;
     - (iii) denoising the received PCG acoustic signals by:
       - (1) applying a band-pass filter with cutoff frequencies of 25 Hz and 140 Hz to the PCG acoustic signals;
       - (2) estimating a spectral noise spectrum during brief pauses in heart sound activity; and
       - (3) subtracting the estimate from a spectrum of the whole signal to obtain a clean heart sound signal;
     - (iv) processing the PCG signals into one or more of temporal features, amplitude features, frequency features, or spectral entropy features for each heartbeat of the subject; and
     - (v) converting the processed features into one or more proxy metrics of cardiac tissue and valvular blood flow parameters with a set of predetermined conversion equations.

2. The system of claim 1, wherein said instructions when, executed by the processor, further perform steps comprising:
   - identifying start and end times of individual heartbeats in PCG signals using ECG signals as a reference;
   - identifying first (S1) and second (S2) heart sounds, and diastolic and systolic intervals within each identified heartbeat; and
   - assessing whether a heartbeat qualifies as a quality heartbeat by determining whether both S1 and S2 have been successfully identified, determining whether systolic and diastolic intervals are free of signal excursions, and determining whether the heartbeat duration is within ±20% of median duration for the subject.

3. The system of claim 1, wherein said amplitude feature processing comprises:
   - applying a Hilbert transform on the PCG signal with signal processing in both the time and frequency domains;
   - applying a low-pass filter with cutoff frequency of 51 Hz, thereby producing a signal envelope, and
   - calculating the 60th percentile value of the resulting signal envelope for that heartbeat.

4. The system of claim 1, wherein said frequency feature processing comprises:
   - isolating a PCG signal corresponding to one heartbeat;
   - applying a Hamming window to a segment of the PCG signal;
   - applying a 64-point discrete Fourier transform, and
   - calculating a center of mass of a frequency distribution between 16 Hz and 160 Hz for the heartbeat.

5. The system of claim 1, wherein said spectral entropy frequency feature processing comprises:
   - isolating a PCG signal corresponding to one heartbeat;
   - obtaining a signal distribution probability estimate from the PCG signal; and
   - calculating a negative product of the signal probability distribution estimate with its logarithm for that heartbeat.

6. The system of claim 1, wherein each conversion equation is generated using linear regression applied to a training dataset of subject condition ground truth data and sensor signal data obtained for a subject population.

7. The system of claim 1, wherein the calculation of a PCG-based proxy metric for echocardiogram-based peak E velocity parameter comprises:
   - obtaining denoised PCG signals for diastolic intervals;
   - identifying quality heartbeats;
   - calculating ratios of amplitude feature values for pulmonic and aortic signals of each heartbeat;
   - calculating a mean of available ratios across all quality heartbeats for each subject; and fitting the calculated mean to a pre-defined linear model using a pre-determined conversion equation.

8. The system of claim 1, wherein the calculation of a PCG-based proxy metric for the echocardiogram-based E/A ratio parameter comprises:

obtaining raw pulmonic PCG signals for quality heartbeats;

calculating ratios of spectral entropy feature values for early and late diastolic intervals of each heartbeat;

calculating the mean of the available ratios across all quality heartbeats for each subject; and fitting the calculated mean to a pre-defined linear model using a pre-determined conversion equation.

9. The system of claim 1, wherein the calculation of a PCG-based proxy metric for the echocardiogram-based e' velocity parameter comprises:

obtaining denoised aortic PCG signals for all heartbeats;

calculating frequency feature values for late systolic intervals of each heartbeat;

calculating a mean of available ratios across all heartbeats for each subject; and fitting the calculated mean to a pre-defined linear model using a pre-determined conversion equation.

10. The system of claim 1, wherein the calculation of a PCG-based proxy metric for the echocardiogram-based peak TR velocity parameter comprises:

obtaining denoised PCG signals for diastolic intervals of quality heartbeats;

calculating ratios of spectral entropy feature values for pulmonic and aortic signals of each heartbeat;

calculating the mean of available ratios across all quality heartbeats for each subject; and fitting the calculated mean to a pre-defined linear model using a pre-determined conversion equation.

11. The system of claim 1, wherein the calculation of a PCG-based proxy metric for the echocardiography-based LAVi parameter comprises:

obtaining raw mitral PCG signals for all heartbeats;

calculating frequency feature values for early diastolic intervals of each heartbeat;

calculating the mean of available ratios across all heartbeats for each subject; and fitting the calculated mean to a pre-defined linear model using a pre-determined conversion equation.

12. The system of claim 1, wherein the PCG-based proxy metrics for peak E velocity, e' velocity, LAVi, E/A ratio, and peak TR velocity are output to a diagnostic processor configured for assessing diastolic function and left atrial pressure from the PCG-based proxy metrics.

13. A method for computing proxy metrics for echocardiographic parameters, the method comprising:

(a) receiving PCG acoustic signals from one or more sensors attached to a subject;

(b) receiving simultaneously electrocardiogram (ECG) signals from one or more sensors attached to the subject;

(c) processing the denoised PCG signals into one or more of temporal features, amplitude features, frequency features, or spectral entropy features for each heartbeat of the same subject;

(d) converting the extracted features into a plurality of cardiac tissue and valvular blood flow parameter analogues (proxy metrics) based on a set of predetermined conversion equations, said conversions comprising;

(i) processing the amplitude features for all heartbeats of the same subject into a proxy metric for the peak velocity of blood flow through the subject's mitral valve during early diastole (peak E velocity);

(ii) processing the frequency features for all heartbeats of the same subject into proxy metrics for the average flow velocity through the subject's mitral valve during early diastole (e' velocity) and the maximum volume of the subject's left atrium indexed to the subject's body surface area (LAVi); and (iii) processing the spectral entropy features for all heartbeats of the same subject into a proxy metric for the ratio of early-to-late peak flow velocities through the subject's mitral valve during diastole (E/A ratio) and the peak velocity of blood backflow through the subject's tricuspid valve during systole (peak TR velocity).

14. The method of claim 13, further comprising denoising of the received PCG acoustic signals, said denoising comprising:

applying a band-pass filter with cutoff frequencies of 25 Hz and 140 Hz to the PCG acoustic signals;

estimating a spectral noise spectrum during brief pauses in heart sound activity; and subtracting the estimate from a spectrum of the whole signal to obtain a clean heart sound signal.

15. The method of claim 13, further comprising:

identifying start and end times of individual heartbeats in PCG signals using ECG signals as a reference;

identifying first (S1) and second (S2) heart sounds, and diastolic and systolic intervals within each identified heartbeat; and assessing whether a heartbeat qualifies as a quality heartbeat by determining whether both S1 and S2 have been successfully identified, determining whether systolic and diastolic intervals are free of signal excursions, and determining whether the heartbeat duration is within ±20% of median duration for the subject.

16. The method of claim 13, wherein said amplitude feature processing comprises:

applying a Hilbert transform on the PCG signal with signal processing in both the time and frequency domains;

applying a low-pass filter with cutoff frequency of 51 Hz, thereby producing a signal envelope, and calculating the 60th percentile value of the resulting signal envelope for that heartbeat.

17. The method of claim 13, wherein said frequency feature processing comprises:

isolating a PCG signal corresponding to one heartbeat;

applying a Hamming window to a segment of the PCG signal;

applying a 64-point discrete Fourier transform, and calculating a center of mass of a frequency distribution between 16 Hz and 160 Hz for the heartbeat.

18. The method of claim 13, wherein said spectral entropy frequency feature processing comprises:

isolating a PCG signal corresponding to one heartbeat;

obtaining a signal distribution probability estimate from the PCG signal; and calculating a negative product of the signal probability distribution estimate with its logarithm for that heartbeat.

19. The method of claim 13, wherein the calculation of a PCG-based proxy metric for echocardiogram-based peak E velocity parameter comprises:

obtaining denoised PCG signals for diastolic intervals;

identifying quality heartbeats;

calculating ratios of amplitude feature values for pulmonic and aortic signals of each heartbeat;

calculating a mean of available ratios across all quality heartbeats for each subject; and fitting the calculated mean to a pre-defined linear model using a pre-determined conversion equation.

20. The method of claim 13, wherein the calculation of a PCG-based proxy metric for the echocardiogram-based E/A ratio parameter comprises:

obtaining raw pulmonic PCG signals for quality heartbeats;

calculating ratios of spectral entropy feature values for early and late diastolic intervals of each heartbeat;

calculating the mean of the available ratios across all quality heartbeats for each subject; and fitting the calculated mean to a pre-defined linear model using a pre-determined conversion equation.

21. The method of claim 13, wherein the calculation of a PCG-based proxy metric for the echocardiogram-based e' velocity parameter comprises:

obtaining denoised aortic PCG signals for all heartbeats;

calculating frequency feature values for late systolic intervals of each heartbeat;

calculating a mean of available ratios across all heartbeats for each subject; and fitting the calculated mean to a pre-defined linear model using a pre-determined conversion equation.

22. The method of claim 13, wherein the calculation of a PCG-based proxy metric for the echocardiogram-based peak TR velocity parameter comprises:

obtaining denoised PCG signals for diastolic intervals of quality heartbeats;

calculating ratios of spectral entropy feature values for pulmonic and aortic signals of each heartbeat;

calculating the mean of available ratios across all quality heartbeats for each subject; and fitting the calculated mean to a pre-defined linear model using a pre-determined conversion equation.

23. The method of claim 13, wherein the calculation of a PCG-based proxy metric for the echocardiography-based LAVi parameter comprises:

obtaining raw mitral PCG signals for all heartbeats;

calculating frequency feature values for early diastolic intervals of each heartbeat;

calculating the mean of available ratios across all heartbeats for each subject; and fitting the calculated mean to a pre-defined linear model using a pre-determined conversion equation.

* * * * *